US008394606B2

(12) United States Patent  
Ali et al.

(10) Patent No.: US 8,394,606 B2  
(45) Date of Patent: Mar. 12, 2013

(54) NEUTROPHIL GELATINASE-ASSOCIATED LIPOCALIN (NGAL) PROTEIN ISOFORMS ENRICHED FROM URINE AND RECOMBINANT CHINESE HAMSTER OVARY (CHO) CELLS AND RELATED COMPOSITIONS, ANTIBODIES, AND METHODS OF ENRICHMENT, ANALYSIS AND USE

(75) Inventors: Salman Ali, Hoffman Estates, IL (US); Ryan M. Bonn, Kenosha, WI (US); Frank C. Grenier, Libertyville, IL (US); Tracey D. Rae, Glenview, IL (US); Kevin R. Rupprecht, Gurnee, IL (US); Hina N. Syed, Gurnee, IL (US); Bailin Tu, Libertyville, IL (US); Joan D. Tyner, Beach Park, IL (US); Ryan F. Workman, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 150 days.

(21) Appl. No.: 12/612,061

(22) Filed: Nov. 4, 2009

(65) Prior Publication Data

US 2010/0116662 A1 May 13, 2010

Related U.S. Application Data

(60) Provisional application No. 61/111,551, filed on Nov. 5, 2008.

(51) Int. Cl.
*C07K 1/14* (2006.01)
(52) U.S. Cl. .................... 435/69.1; 530/424
(58) Field of Classification Search ............... None
See application file for complete search history.

(56) References Cited

U.S. PATENT DOCUMENTS

| | | | |
|---|---|---|---|
| 5,627,034 | A | 5/1997 | Gould et al. |
| 5,846,739 | A | 12/1998 | Gould et al. |
| 6,528,286 | B1 | 3/2003 | Ryll |
| 7,153,660 | B2 | 12/2006 | Moses et al. |
| 2006/0008804 | A1 | 1/2006 | Chibout et al. |
| 2007/0037232 | A1 | 2/2007 | Barasch et al. |
| 2007/0105166 | A1 | 5/2007 | Moses et al. |
| 2007/0166765 | A1 | 7/2007 | Rohlff |
| 2007/0196876 | A1 | 8/2007 | Moses et al. |
| 2007/0254290 | A1 | 11/2007 | Yen et al. |
| 2007/0254370 | A1 | 11/2007 | Devarajan et al. |
| 2008/0014604 | A1 | 1/2008 | Devarajan et al. |
| 2008/0014644 | A1 | 1/2008 | Barasch et al. |
| 2008/0090304 | A1 | 4/2008 | Barasch et al. |
| 2009/0124022 | A1 | 5/2009 | Birkenmeyer et al. |
| 2009/0176274 | A1* | 7/2009 | Tu et al. ............ 435/69.1 |
| 2009/0269777 | A1 | 10/2009 | Birkenmeyer et al. |
| 2010/0304413 | A1 | 12/2010 | Uttenthal et al. |
| 2011/0287455 | A1 | 11/2011 | Venge |

FOREIGN PATENT DOCUMENTS

| | | |
|---|---|---|
| WO | WO2004005540 A2 | 1/2004 |
| WO | WO2006066587 A1 | 6/2006 |
| WO | WO2006086638 A2 | 8/2006 |
| WO | WO2007044994 A2 | 4/2007 |
| WO | WO2007047458 A2 | 4/2007 |
| WO | WO2009052390 A1 | 4/2009 |
| WO | WO2009052392 A1 | 4/2009 |
| WO | WO2009052400 A1 | 4/2009 |
| WO | WO2009062520 A1 | 5/2009 |
| WO | WO2010054025 A1 | 5/2010 |

OTHER PUBLICATIONS

Bonn R., et al., "P23. Analysis of Global Isoform Distribution of Human NGAL Proteins" [online], [retrieved on Mar. 29, 2010]. Retrieved from the Internet: <http://www.isppp.org/ISPPP_2009_Abstracts_posters.pdf>.
Bundgaard J.R., et al., "Molecular Cloning and Expression of a cDNA Encoding NGAL: A Lipocalin Expressed in Human Neutrophils," Biochemical and Biophysical Research Communications, 1994, vol. 202 (3), pp. 1468-1475.
Fang W.K., et al., "A Novel Alternative Spliced Variant of Neutrophil Gelatinase-Associated Lipocalin Receptor in Oesophageal Carcinoma Cells," Biochem. J., 2007, vol. 403 (2), pp. 297-303.
Grenier F., et al., "Multi-Site Evaluation of an Assay in Development for NGAL (Neutrophil Gelatinase-Associated Lipocalin) on the Abbott ARCHITECT® Analyzer," Clinical Chemistry, 2008, vol. 54 (6), pp. A170.
PCT International Application No. PCT/US2009/063319, International Search Report and Written Opinion, mailed on Apr. 22, 2010, 23 pages (Abbott's Reference No. 9600W001).

(Continued)

*Primary Examiner* — Jeffrey E Russel
(74) *Attorney, Agent, or Firm* — Audrey L. Bartnicki; Carol Larcher; Larcher & Chao Law Group

(57) ABSTRACT

A composition comprising neutrophil gelatinase-associated lipocalin (NGAL), which has been enriched from urine, has a molecular weight of about 24.9 kDa to about 25.9 kDa, and comprises a plurality of isoforms having isoelectric points (pIs) ranging from about 5.9 to about 9.1; a composition comprising NGAL, which has been enriched from recombinant Chinese hamster ovary (CHO) cells, has a molecular weight of about 25.9 kDa to about 27.9 kDa, and comprises a plurality of isoforms having pIs ranging from about 5.6 to about 9.1; a method of obtaining from urine a composition comprising a plurality of isoforms of NGAL, which method comprises enriching NGAL in urine without separating molecules based on charge; a method of obtaining from recombinant CHO cells a composition comprising a plurality of isoforms of NGAL, which method comprises enriching NGAL in a composition without separating molecules based on charge; and a method of analyzing NGAL isoforms enriched from urine or recombinant CHO cells comprising analyzing an enriched composition comprising NGAL isoforms by two-dimensional electrophoresis and Western blot.

6 Claims, No Drawings

OTHER PUBLICATIONS

Kjeldsen L., et al., "Isolation and Primary Structure of NGAL, a Novel Protein Associated with Human Neutrophil Gelatinase," The Journal of Biological Chemistry, 1993, vol. 268 (14), pp. 10425-10432.

Lafon-Cazal M., et al., "Proteomic Analysis of Astrocytic Secretion in the Mouse. Comparison with the Cerebrospinal Fluid Proteome," Journal of Biological Chemistry, 2003, vol. 278 (27), pp. 24438-24448.

Monier F., et al., "Gelatinase Isoforms in Urine from Bladder Cancer Patients," Clinica Chimica Acta, 2000, vol. 299 (1-2), pp. 11-23.

PCT International Application No. PCT/US2009/063319, Invitation to Pay Additional Fees and, Where Applicable, Protest Fee, Date Mailed Apr. 4, 2010, 8 pages (Abbott's Reference No. 9600WOO1).

Rae, et al., "Structural Properties of Human Urine-Sourced Neutrophil Gelatinase Associated Lipocalin (huNGAL)" [online] FASEB 2009 [retrieved on Apr. 2009]. Retrieved from the Internet: (URL:http://www.fasebj.org/cgi/content/meet ing_abstract/23/1 MeetingAbstracts/863.10).

Roudkenar M.H., et al., "Neutrophil Gelatinase-Associated Lipocalin Acts as a Protective Factor Against H202 Toxicity," Archives of Medical Research, 2008, vol. 39 (6), pp. 560-566.

Rudd P.M., et al., "Glycosylation of Natural Human Neutrophil Gelatinase B and Neutrophil Gelatinase B-Associated Lipocalin," Biochemistry, 1999, vol. 38 (42), pp. 13937-13950.

Kjeldsen L., et al., "Human neutrophil gelatinase: A marker for circulating blood neutrophils. Purification and quantitation by enzyme linked immunosorbent assay," Eur. J. Haematology, 1992, 49, pp. 180-191.

* cited by examiner

SEQUENCE LISTING

```
<160> NUMBER OF SEQ ID NOS: 6

<210> SEQ ID NO 1
<211> LENGTH: 198
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: The first 20 amino acids are the signal peptide
      which would be labeled 1 to 20, with Gln (at position 21) being
      considered the first amino acid of the mature NGAL peptide
```

```
<400> SEQUENCE: 1

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly
        195

<210> SEQ ID NO 2
<211> LENGTH: 178
<212> TYPE: PRT
<213> ORGANISM: Artificial sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Gln can be preceded by a Met residue (e.g.,
      when synthetic and/or produced in prokaryotes.
<220> FEATURE:
<221> NAME/KEY: MISC_FEATURE
<222> LOCATION: (178)..(178)
<223> OTHER INFORMATION: Can, optionally, be succeeded at the C-terminus
      by one or more His residues, and especially, 6 His residues
      (HHHHHH).

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95
```

```
Ile Lys Ser Tyr Pro Gly Leu Thr Ser Tyr Leu Val Arg Val Val Ser
            100                 105                 110

Thr Asn Tyr Asn Gln His Ala Met Val Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 3
<211> LENGTH: 612
<212> TYPE: DNA
<213> ORGANISM: Homo sapiens

<400> SEQUENCE: 3
atgcccctag gtctcctgtg gctgggccta gccctgttgg gggctctgca tgcccaggcc      60
caggactcca cctcagacct gatcccagcc ccacctctga gcaaggtccc tctgcagcag     120
aacttccagg acaaccaatt ccaggggaag tggtatgtgg taggcctggc agggaatgca     180
attctcagag aagacaaaga cccgcaaaag atgtatgcca ccatctatga gctgaaagaa     240
gacaagagct acaatgtcac ctccgtcctg tttaggaaaa agaagtgtga ctactggatc     300 aggactttg ttccaggttg ccagcccggc gagttcacgc tgggcaacat taagagttac     360
cctggattaa cgagttacct cgtccgagtg gtgagcacca actacaacca gcatgctatg     420
gtgttcttca gaaagtttc tcaaaacagg gagtacttca gatcaccct ctacggggaga     480 accaaggagc tgacttcgga actaaaggag aacttcatcc gcttctccaa atctctgggc     540
ctccctgaaa accacatcgt cttccctgtc ccaatcgacc agtgtatcga cggccatcat     600
caccatcacc at                                                        612

<210> SEQ ID NO 4
<211> LENGTH: 198
<212> TYPE: PRT
<213> ORGANISM: Artificial sequence
<220> FEATURE:
<223> OTHER INFORMATION: Chemically synthesized
<220> FEATURE:
<221> NAME/KEY: MISC_FEATURE
<222> LOCATION: (1)..(20)
<223> OTHER INFORMATION: The first 20 amino acids are the signal peptide
      which would be labeled -1 to -20, with Gln (at position 21) being
      considered amino acid 1 of the NGAL peptide

<400> SEQUENCE: 4

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95
```

```
Asp Tyr Trp Ile Arg Thr Phe Val Pro Gly Ser Gln Pro Gly Glu Phe
                100                 105                 110

Thr Leu Gly Asn Ile Lys Ser Tyr Pro Gly Leu Thr Ser Tyr Leu Val
            115                 120                 125

Arg Val Val Ser Thr Asn Tyr Asn Gln His Ala Met Val Phe Phe Lys
        130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly
        195

<210> SEQ ID NO 5
<211> LENGTH: 178
<212> TYPE: PRT
<213> ORGANISM: Artificial sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Gln can be preceded by a Met residue (e.g.,
      when synthetic and/or produced in prokaryotes)
<220> FEATURE:
<221> NAME/KEY: MISC_FEATURE
<222> LOCATION: (178)..(178)
<223> OTHER INFORMATION: Can, optionally, be succeeded at the C-terminus
      by one or more His residues, and especially, 6 His residues
      (HHHHHH).

<400> SEQUENCE: 5

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

```
<210> SEQ ID NO 6
<211> LENGTH: 552
<212> TYPE: DNA
<213> ORGANISM: Artificial sequence
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: Optionally, can be preceded at the N-terminus
      by an initiation codon encoding Met, namely, an ATG.

<400> SEQUENCE: 6
caggactcca cctcagacct gatcccagcc ccacctctga gcaaggtccc tctgcagcag      60
aacttccagg acaaccaatt ccaggggaag tggtatgtgg taggcctggc agggaatgca     120
attctcagag aagacaaaga cccgcaaaag atgtatgcca ccatctatga gctgaaagaa     180
gacaagagct acaatgtcac ctccgtcctg tttaggaaaa agaagtgtga ctactggatc     240
aggacttttg ttccaggttc gcagcccggc gagttcacgc tgggcaacat taagagttac     300
cctggattaa cgagttacct cgtccgagtg gtgagcacca actacaacca gcatgctatg     360
gtgttcttca agaaagtttc tcaaaacagg gagtacttca agatcaccct ctacgggaga     420
accaaggagc tgacttcgga actaaaggag aacttcatcc gcttctccaa atctctgggc     480
ctccctgaaa accacatcgt cttccctgtc ccaatcgacc agtgtatcga cggccatcat     540
caccatcacc at                                                        552
```

NEUTROPHIL GELATINASE-ASSOCIATED LIPOCALIN (NGAL) PROTEIN ISOFORMS ENRICHED FROM URINE AND RECOMBINANT CHINESE HAMSTER OVARY (CHO) CELLS AND RELATED COMPOSITIONS, ANTIBODIES, AND METHODS OF ENRICHMENT, ANALYSIS AND USE

RELATED APPLICATION INFORMATION

This application claims the priority of Provisional U.S. Patent Application Ser. No. 61/111,551 filed on Nov. 5, 2008, incorporated by reference in its entirety.

TECHNICAL FIELD

The present disclosure relates to isoforms of NGAL in urine and in an enriched composition obtained from CHO cells that recombinantly produce NGAL, a composition comprising one or more isoforms of NGAL, anti-NGAL antibodies, a method of enriching NGAL isoforms without separating molecules based on charge, a method of analyzing NGAL isoforms, a method of assaying a test sample for one or more isoforms of NGAL, and a method of prophylactic/therapeutic treatment, among others.

BACKGROUND

Lipocalins are a family of extracellular ligand-binding proteins that are found in a variety of organisms from bacteria to humans. Lipocalins possess many different functions, such as the binding and transport of small hydrophobic molecules, nutrient transport, cell growth regulation, and modulation of the immune response, inflammation and prostaglandin synthesis. Moreover, some lipocalins are also involved in cell regulatory processes and serve as diagnostic and prognostic markers in a variety of disease states. For example, the plasma level of α-glycoprotein is monitored during pregnancy and in the diagnosis and prognosis of conditions such as cancer (e.g., cancer being treated with chemotherapy), renal dysfunction, myocardial infarction, arthritis, and multiple sclerosis.

Neutrophil gelatinase-associated lipocalin (NGAL), which is also known as human neutrophil lipocalin (HNL), N-formyl peptide binding protein, and 25 kDa α2-microglobulin-related protein, is a 24 kDa protein, which can exist as a monomer, a homodimer, or a heterodimer with proteins, such as gelatinase B or matrix metalloproteinase-9 (MMP-9). A trimeric form of NGAL also has been identified. NGAL is secreted from specific granules of activated human neutrophils. Homologous proteins have been identified in mouse (24p3/uterocalin) and rat (α2-microglobulin-related protein/neu-related lipocalin). Structural data have confirmed NGAL has an eight-stranded β-barrel structure, which is characteristic of lipocalins; however, NGAL has an unusually large cavity lined with more polar and positively charged amino acid residues than normally seen in lipocalins. NGAL is believed to bind small lipophilic substances, such as bacteria-derived lipopolysaccharides and formyl peptides, and may function as a modulator of inflammation.

NGAL is an early marker for acute renal injury or disease. In addition to being secreted by specific granules of activated human neutrophils, NGAL is also produced by nephrons in response to tubular epithelial damage and is a marker of tubulointerstitial (TI) injury. NGAL levels rise in acute tubular necrosis (ATN) from ischemia or nephrotoxicity, even after mild "subclinical" renal ischemia. Moreover, NGAL is known to be expressed by the kidney in cases of chronic kidney disease (CKD) and acute kidney injury ((AKI); see, e.g., Devarajan et al., Amer. J. Kidney Diseases 52(3); 395-399 (September 2008); and Bolignano et al., Amer. J. Kidney Diseases 52(3): 595-605 (September 2008)). Elevated urinary NGAL levels have been suggested as predictive of progressive kidney failure. It has been previously demonstrated that NGAL is markedly expressed by kidney tubules very early after ischemic or nephrotoxic injury in both animal and human models. NGAL is rapidly secreted into the urine, where it can be easily detected and measured, and precedes the appearance of any other known urinary or serum markers of ischemic injury. The protein is resistant to proteases, suggesting that it can be recovered in the urine as a faithful marker of NGAL expression in kidney tubules. Further, NGAL derived from outside of the kidney, for example, filtered from the blood, does not appear in the urine, but rather is quantitatively taken up by the proximal tubule. NGAL is also a marker in the diagnosis and/or prognosis of a number of other diseases (see, e.g., Xu et al., Biochim. et Biophys. Acta 1482: 298-307 (2000)), disorders, and conditions, including inflammation, such as that associated with infection. It is a marker for irritable bowel syndrome (see, e.g., U.S. Pat. App. Pub. Nos. 2008/0166719 and 2008/0085524); renal disorders, diseases and injuries (see, e.g., U.S. Pat. App. Pub. Nos. 2008/0090304, 2008/0014644, 2008/0014604, 2007/0254370, and 2007/0037232); systemic inflammatory response syndrome (SIRS), sepsis, severe sepsis, septic shock and multiple organ dysfunction syndrome (MODS) (see, e.g., U.S. Pat. App. Pub. Nos. 2008/0050832 and 2007/0092911; see, also, U.S. Pat. No. 6,136,526); periodontal disease (see, e.g., U.S. Pat. No. 5,866,432); and venous thromboembolic disease (see, e.g., U.S. Pat. App. Pub. Nos. 2007/0269836), among others. In its free, uncomplexed form it is a marker for ovarian cancer, invasive and noninvasive breast cancer, and atypical ductal hyperplasia, which is a major risk factor for breast cancer (see, e.g., U.S. Pat. App. Pub. No. 2007/0196876; see, also, U.S. Pat. Nos. 5,627,034 and 5,846,739 with regard to assessing the proliferative status of a carcinoma). It also is a marker for colon (Nielsen et al., Gut 38: 414-420 (1996)), pancreatic (Furutani et al., Cancer Lett. 122: 209-214 (1998)), and esophageal cancer (see, e.g., Zhang et al., J. Clin. Pathol. (2006)). When complexed with MMP-9, it also is a marker for conditions associated with tissue remodeling (see, e.g., U.S. Pat. App. Pub. No. 2007/0105166 and U.S. Pat. No. 7,153,660). A high level of NGAL (e.g., approximately 350 μg/L (Xu et al., Scand. J. Clin. Lab. Invest. 55: 125-131 (1995)) also can be indicative of a bacterial infection as opposed to a viral infection (see, e.g., U.S. Pat. App. Pub. No. 2004/0115728).

A variety of immunoassays are known in the art for detecting NGAL. Such immunoassays can be used, for example, to diagnose, prognosticate, and/or assess the efficacy of prophylactic/therapeutic treatment of a given condition, disease or disorder, such as those discussed above. Until the present disclosure, however, it has not been appreciated that different isoforms of NGAL exist in urine. It also has not been appreciated that a plurality of isoforms of NGAL can be enriched from CHO cells that recombinantly express NGAL. The present disclosure seeks to provide a composition comprising a plurality of isoforms of NGAL, as well as a method of obtaining such a composition from urine and recombinant CHO cells, and a method of analyzing NGAL isoforms enriched from urine and recombinant CHO cells. Additional objects, as well as advantages, and inventive features of the present disclosure, will be apparent from the detailed description provided herein.

SUMMARY

A composition comprising neutrophil gelatinase-associated lipocalin (NGAL), which has been enriched from urine, is provided. The NGAL has a molecular weight of about 24.9 kDa to about 25.9 kDa, and comprises a plurality of isoforms having isoelectric points (pIs) ranging from about 5.9 to about 9.1.

A composition comprising NGAL, which has been enriched from a composition, which has been obtained from Chinese hamster ovary (CHO) cells that recombinantly produce NGAL, is also provided. The NGAL has been enriched by (a) acidification and (b) extraction with ethanol and zinc acetate, and (c) in the absence of separation of molecules based on charge, ultra-filtration buffer exchange, size-exclusion chromatography, and/or ammonium sulfate precipitation. The NGAL has a molecular weight of about 25.9 kDa to about 27.9 kDa, and comprises a plurality of isoforms having pIs ranging from about 5.6 to about 9.1.

Further provided is a method of obtaining from urine a composition comprising a plurality of isoforms of NGAL. The method comprises enriching NGAL in urine without separating molecules based on charge.

Still further provided is a method of obtaining from CHO cells that recombinantly produce NGAL a composition comprising a plurality of isoforms of NGAL. The method comprises enriching NGAL in a composition, which is obtained from CHO cells that recombinantly produce NGAL, without separating molecules based on charge, by acidifying the composition and extracting the composition with ethanol and zinc acetate.

A method of analyzing NGAL isoforms enriched from urine is provided. The method comprises analyzing a composition comprising NGAL isoforms enriched from urine by two-dimensional electrophoresis and Western blot.

A method of analyzing NGAL isoforms enriched from CHO cells that recombinantly produce NGAL is also provided. The method comprises analyzing a composition comprising NGAL isoforms enriched from CHO cells that recombinantly produce NGAL by two-dimensional electrophoresis and Western blot.

DETAILED DESCRIPTION

The present disclosure is predicated, at least in part, on the surprising and unexpected discovery of similar neutrophil gelatinase-associated lipocalin (NGAL) isoforms in human urine and Chinese hamster ovary (CHO) cells that recombinantly produce NGAL. NGAL isoforms having a pI ranging from 6.7 to 8.9 have been found in media of cultured astrocytes from the central nervous system (see, e.g., Lafon-Cazol et al., J. Biol. Chem. 278(27): 24438-24448 (2003)); however, there are no clear prior reports of the presence of NGAL isoforms in urine and recombinant CHO cells that recombinantly produce NGAL. pI values of 6.9, 8.2 and 8.8-9.2 have been previously reported for kidney NGAL isolated from the urine of patients having acute kidney injury and chronic renal disease (see, e.g., PCT International Application WO 2007/047458, paragraph 0068).

Definitions (a) "Neutrophil gelatinase-associated lipocalin (NGAL)," which is also known as human neutrophil lipocalin (HNL), N-formyl peptide binding protein, and 25 kDa α2-microglobulin-related protein, is a 24 kDa protein, which can exist as a monomer, a homodimer, or a heterodimer with proteins, such as gelatinase B or matrix metalloproteinase-9 (MMP-9). See, e.g., Kjeldsen et al., J. Biol. Chem. 268 (14): 15 10425-10432 (1993), for an exemplary amino acid sequence. While a signal peptide may or may not be present, generally, when present, the signal peptide comprises amino acids 1-20. Therefore, all amino acid sequences are numbered herein from the N-terminus to the C-terminus with the signal peptide present. If the signal peptide is not present, the first amino acid is numbered 21.

The NGAL polynucleotide or polypeptide can be any NGAL sequence, e.g., including that set forth as Genbank accession numbers Genpept CAA58127 (SEQ ID NO:1), AAB26529, XP_862322, XP_548441, P80108, P11672, X83006.1, X99133.1, CAA67574.1, BC033089.1, AAH33089.1, S75256.1, AD14168.1, JC2339, 1DFVA, 1DFVB, 1L6MA, 1L6MB, 1L6MC, 1NGLA, 1QQSA, 1X71A, 1X71B, 1X71C, 1X89A, 1X89B, 1X89C, 1X8UA, 1X8UB, and 1X8UC. NGAL polynucleotide and polypeptide (e.g., polyamino acid) sequences are as found in nature, based on sequences found in nature, isolated, synthetic, semi-synthetic, recombinant, or other. In one embodiment, the NGAL is human NGAL (also known as "hNGAL"). NGAL polypeptide sequences can be of the mature human NGAL sequence (sequence not including the 20-residue amino acid signal peptide typically found in nature, and/or minus any other signal peptide sequence). When a signal peptide is present, it is numbered, e.g., as residues 1 to 20, with comparable numbering applied for the encoding polynucleotide sequence.

Likewise, an initial Met residue at the N-terminus of NGAL is present only in NGAL produced in prokaryotes (e.g., E. coli), or in synthetic (including semi-synthetic) or derived sequences, and not in NGAL produced in eukaryotes (e.g., mammalian cells, including human and yeast cells). Consequently, when present, an initial Met residue is typically counted as a negative number, e.g., as residue −1, with no similar numbering adjustment being made for the polynucleotide sequence in a prokaryotic versus eukaryotic background or expression system inasmuch as the polynucleotide sequence is replicated and transcribed the same in both backgrounds, and the difference lies at the level of translation.

Accordingly, the disclosure herein encompasses a multitude of different NGAL polynucleotide and polypeptide sequences as present and/or produced in a prokaryotic and/or eukaryotic background (e.g., with consequent optimization for codon recognition). In sum, the sequences may or may not possess or encode: (a) a signal peptide; (b) an initiator Met residue present in the mature NGAL sequence at the N-terminus; (c) an initiator Met residue present at the start of a signal peptide that precedes the mature NGAL protein; and (d) other variations such as would be apparent to one skilled in the art.

Exemplary sequences include, but are not limited to, those as set forth herein: SEQ ID NO:1 (wild-type NGAL polypeptide including signal peptide); SEQ ID NO:2 (wild-type NGAL polypeptide not including any signal peptide; can be preceded by a Met initiator residue when produced in prokaryotes and a Met initiator codon is present; however, there is no Met initiator residue when produced in eukaryotes, regardless of whether a Met initiator codon is present); and SEQ ID NO:3 (wild-type NGAL polynucleotide sequence including that encoding a signal peptide). Exemplary sequences further include any mutant sequences set forth in any one or more of U.S. Provisional Pat. App. Nos. 60/981,470, 60/981,471 and 60/981,473, all filed on Oct. 19, 2007, and U.S. patent application Ser. Nos. 12/104,408, 12/104,410, and 12/104,413, all filed on Apr. 16, 2008, each of which is incorporated by reference in its entirety for its teachings regarding same.

(b) "NGAL fragment" refers to a polypeptide that comprises a part that is less than the entirety of a mature NGAL (e.g., human NGAL) or NGAL including a signal peptide. In particular, a NGAL fragment comprises from about 5 to about 178 or about 179 contiguous amino acids of SEQ ID NO: 1 or 2, for example. In particular, an NGAL fragment comprises from about 5 to about 170 contiguous amino acids of SEQ ID NO: 1 or 2. In particular, an NGAL fragment comprises at least about 5 contiguous amino acid residues of SEQ ID NO: 1 or 2, at least about 10 contiguous amino acid residues of SEQ ID NO: 1 or 2, at least about 15 contiguous amino acid residues of SEQ ID NOS:1 or 2, at least about 20 contiguous amino acid residues of SEQ ID NO: 1 or 2, at least about 25 contiguous amino acid residues of SEQ ID NO: 1 or 2, at least about 30 contiguous amino acid residues of SEQ ID NO: 1 or 2, at least about 35 contiguous amino acid residues of SEQ ID NO: 1 or 2, at least about 40 contiguous amino acid residues of SEQ ID NO: 1 or 2, at least about 45 contiguous amino acid residues of SEQ ID NO: 1 or 2, at least about 50 contiguous amino acid residues of SEQ ID NO: 1 or 2, at least about 55 contiguous amino acid residues of SEQ ID NO: 1 or 2, at least about 60 contiguous amino acid residues of SEQ ID NO: 1 or 2, at least about 65 contiguous amino acid residues of SEQ ID NO:1 or 2, at least about 70 contiguous amino acid residues of SEQ ID NO: 1 or 2, at least about 75 contiguous amino acid residues of SEQ ID NO: 1 or 2, at least about 80 contiguous amino acid residues of SEQ ID NO: 1 or 2, at least about 85 contiguous amino acid residues of SEQ ID NO: 1 or 2, at least about 90 contiguous amino acid residues of SEQ ID NO: 1 or 2, at least about 95 contiguous amino acid residues of SEQ ID NO: 1 or 2, at least about 100 contiguous amino acid residues of SEQ ID NO: 1 or 2, at least about 105 contiguous amino acid residues of SEQ ID NO: 1 or 2, at least about 110 contiguous amino acid residues of SEQ ID NO: 1 or 2, at least about 115 contiguous amino acid residues of SEQ ID NO: 1 or 2, at least about 120 contiguous amino acid residues of SEQ ID NO: 1 or 2, at least about 125 contiguous amino acid residues of SEQ ID NO: 1 or 2, at least about 130 contiguous amino acid residues of SEQ ID NO: 1 or 2, at least about 135 contiguous amino acid residues of SEQ ID NO: 1 or 2, at least about 140 contiguous amino acid residues of SEQ ID NO:1 or 2, at least about 145 contiguous amino acid residues of SEQ ID NO: 1 or 2, at least about 150 contiguous amino acid residues of SEQ ID NO: 1 or 2, at least about 160 contiguous amino acid residues of SEQ ID NO: 1 or 2, at least about 165 contiguous amino acid residues of SEQ ID NO: 1 or 2, at least about 170 contiguous amino acid residues of SEQ ID NO: 1 or 2, or at least about 175 contiguous amino acid residues of SEQ ID NO: 1 or 2. References to SEQ ID NO: 1 or 2 are for purposes of illustration only; it is not intended that "NGAL fragment" be limited to fragments derived from SEQ ID NOS: 1 and 2 only.

A fragment of NGAL contains at least one contiguous or nonlinear epitope of NGAL. The precise boundaries of such an epitope can be confirmed using ordinary skill in the art. The epitope can comprise at least about 5 contiguous amino acids, such as about 10 contiguous amino acids, about 15 contiguous amino acids, or about 20 contiguous amino acids.

(c) "Protein isoforms" refers to variants of a polypeptide that are encoded by the same gene but that differ in their molecular weight (MW) and/or isoelectric point (pI). Protein isoforms can differ in their amino acid composition (e.g., as a result of alternative mRNA or pre-mRNA processing (e.g., alternative splicing or limited proteolysis). Additionally, or alternatively, protein isoforms can differ in post-translational modifications (e.g., glycosylation, acylation, phosphorylation, and the like). Use of "protein isoform" herein is intended to encompass the wild-type polypeptide as well as any variants and fragments of the wild-type polypeptide and variants thereof.

(d) "Antibody" and "antibodies" refer to monoclonal antibodies (mAbs), multispecific antibodies, human antibodies, humanized antibodies (fully or partially humanized), animal antibodies (in one aspect, a bird (for example, a duck or a goose), in another aspect, a shark or a whale, in yet another aspect, a mammal, including a non-primate (for example, a cow, a pig, a camel, a llama, a horse, a goat, a rabbit, a sheep, a hamster, a guinea pig, a cat, a dog, a rat, a mouse, etc.) and a non-human primate (for example, a monkey, such as a cynomologous monkey, a chimpanzee, etc.), recombinant antibodies, chimeric antibodies, single-chain Fvs (scFv), single chain antibodies, single domain antibodies, Fab fragments, F(ab')$_2$ fragments, disulfide-linked Fv (sdFv), and anti-idiotypic (anti-Id) antibodies (including, for example, anti-Id antibodies to antibodies of the present invention), and functionally active epitope-binding fragments of any of the above. In particular, antibodies include immunoglobulin molecules and immunologically active fragments of immunoglobulin molecules, namely, molecules that contain an antigen-binding site. Immunoglobulin molecules can be of any type (for example, IgG, IgE, IgM, IgD, IgA and IgY), class (for example, IgG$_1$, IgG$_2$, IgG$_3$, IgG$_4$, IgA$_1$ and IgA$_2$), or subclass. For simplicity sake, an antibody against an analyte is frequently referred to as being either an "anti-analyte antibody" (e.g., an anti-NGAL antibody) or merely an "analyte antibody" (e.g., an NGAL antibody).

Antibodies directed against the polypeptides as described herein, and methods of making such antibodies using the polypeptides are described in U.S. Provisional Pat. App. No. 60/981,471 filed Oct. 19, 2007 (incorporated by reference for its teachings regarding same). Furthermore, the use of such antibodies (and fragments thereof) and polypeptides (and fragments thereof), e.g., in immunoassays and/or as calibrators, controls, and immunodiagnostic agents, are described in U.S. Provisional Pat. App. No. 60/981,473 filed Oct. 19, 2007 (incorporated by reference for its teachings regarding same).

(e) "Recombinant antibody" and "recombinant antibodies" refer to antibodies prepared by one or more steps, including cloning nucleic acid sequences encoding all or a part of one or more mAbs into an appropriate expression vector by recombinant techniques and subsequently expressing the antibody in an appropriate host cell. The terms include, but are not limited to, recombinantly produced mAbs, chimeric antibodies, humanized antibodies (fully or partially humanized), multi-specific or multi-valent structures formed from antibody fragments, bifunctional antibodies, and other antibodies as described in (d) herein.

(f) "Antibody fragment" and "antibody fragments" refer to a portion of an intact antibody comprising the antigen-binding site or variable region. The portion does not include the constant heavy chain domains (i.e., $C_H2$, $C_H3$ or $C_H4$, depending on the antibody isotype) of the Fc region of the intact antibody. Examples of antibody fragments include, but are not limited to, Fab fragments, Fab' fragments, Fab'-SH fragments, F(ab')$_2$ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region. Such fragments are additionally described above under (d). (g) "Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, and enzymes and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

(h) "Epitope," "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

(i) "Specific" and "specificity" in the context of an interaction between members of a specific binding pair (e.g., an antigen (or fragment thereof) and an antibody (or antigenically reactive fragment thereof)) refer to the selective reactivity of the interaction. The phrase "specifically binds to" and analogous phrases refer to the ability of antibodies (or antigenically reactive fragments thereof) to bind specifically to an antigen, such as a particular isoform of NGAL (or a fragment thereof), and not bind specifically to other antigens, such as other isoforms of NGAL (or fragments thereof).

(j) An "immunodiagnostic reagent" comprises one or more antibodies that specifically bind to a region of an NGAL protein as described herein. Immunodiagnostic agents, are described in U.S. Provisional Pat. App. No. 60/981,473 filed Oct. 19, 2007 (incorporated by reference for its teachings regarding same).

(k) "Component" and "components" refer generally to a capture antibody, a detection antibody, a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a patient urine sample in accordance with the methods described herein and other methods known in the art. Some components can be in solution or lyophilized for reconstitution for use in an assay.

(l) "Sample," "urine sample," and "patient urine sample" may be used interchangeably herein to refer to a sample of urine. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

(m) "Urine component" and "urine components" refer generally to any biological or chemical component(s) that can occur in urine, including, but not limited to, proteins, nucleic acids, fatty acids, cells, bacteria, viruses, chemical compounds, and drugs.

(n) "Control" refers to a composition known to not contain NGAL ("negative control") or to contain NGAL ("positive control"). A positive control can comprise a known concentration of NGAL, such as one or more isoforms of NGAL (or fragments thereof). "Control" and "positive control" may be used interchangeably herein to refer to a composition comprising a known concentration of NGAL. A "positive control" can be used to establish assay performance characteristics and is a useful indicator of the integrity of reagents (e.g., analytes).

(o) "Series of calibrating compositions" refers to a plurality of compositions comprising a known concentration of NGAL, such as one or more isoforms of NGAL (or fragments thereof), wherein each of the compositions differs from the other compositions in the series by the concentration of NGAL. To the extent that each series of calibrating compositions contains only a single (or less than all) isoforms of NGAL, more than one series of calibrating compositions, such as one, two, three, four, five, six, or seven series, can be used.

(p) "Pretreatment reagent" (e.g., lysis, precipitation and/or solubilization reagent) lyses any cells and/or solubilizes any analytes that are present in a test sample. Pretreatment is not necessary for all samples, as described further herein. Among other things, solubilizing the analyte entails release of the analyte from any endogenous binding proteins present in the sample. A pretreatment reagent may be homogeneous (not requiring a separation step) or heterogeneous (requiring a separation step). With use of a heterogeneous pretreatment reagent, there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte. Also, proteases, either alone or in combination with any other pretreatment agents (e.g., solvents, detergents, salts, and the like), can be employed.

(q) "Label" means a moiety attached to an antibody or an analyte to render the reaction between the antibody and the analyte detectable. A label can produce a signal that is detectable by visual or instrumental means. Various labels include signal-producing substances, such as chromogens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein.

(r) "Tracer" means an analyte or analyte fragment conjugated to a label, such as an isoform of NGAL conjugated to a fluorescein moiety, wherein the analyte conjugated to the label can effectively compete with the analyte for sites on an antibody specific for the analyte.

(s) A "solid phase" refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. The solid phase can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

(t) "Subject" and "patient" are used interchangeably irrespective of whether the subject has or is currently undergoing any form of treatment. As used herein, the terms "subject" and "subjects" refer to a mammal, including a non-primate (for example, a cow, a pig, a camel, a llama, a horse, a goat, a rabbit, a sheep, a hamster, a guinea pig, a cat, a dog, a rat, and a mouse), a non-human primate (for example, a monkey, such as a cynomolgous monkey, a chimpanzee, etc.), and a human. Preferably, the subject is a human.

(u) "Renal tubular cell injury" means a renal or kidney failure or dysfunction, either sudden (acute) or slowly declining over time (chronic), that can be triggered by a number of disease or disorder processes. Both acute and chronic forms of renal tubular cell injury can result in a life-threatening metabolic derangement.

(v) An "acute renal tubular cell injury" means acute ischemic renal injury (IRI) or acute nephrotoxic renal injury (NRI). IRI includes, but is not limited to, ischemic injury and chronic ischemic injury, acute renal failure, acute glomerulonephritis, and acute tubulo-interstitial nephropathy. NRI toxicity includes, but is not limited to, sepsis (infection), shock, trauma, kidney stones, kidney infection, drug toxicity, poison toxicity, toxin toxicity, and toxicity resulting from injection with a radiocontrast dye.

(w) "Chronic renal tubular cell injury," "progressive renal disease," "chronic renal disease (CRD)," and "chronic kidney disease (CKD)" are used interchangeably herein and include any kidney condition or dysfunction that occurs over a period of time, as opposed to a sudden event, to cause a gradual decrease of renal tubular cell function or worsening of renal tubular cell injury. One endpoint on the continuum of chronic renal disease is "chronic renal failure (CRF)." For example, chronic kidney disease or chronic renal injury as used interchangeably herein, includes, but is not limited to, conditions or dysfunctions caused by chronic infections, chronic inflammation, glomerulonephritis, vascular diseases, interstitial nephritis, drugs, toxins, trauma, renal stones, long standing hypertension, diabetes, congestive heart failure, nephropathy from sickle cell anemia and other blood dyscrasias, nephropathy related to hepatitis, HIV, parvovirus and BK virus (a human polyomavirus), cystic kidney diseases, congenital malformations, obstruction, malignancy, kidney disease of indeterminate causes, lupus nephritis, membranous glomerulonephritis, membranoproliferative glomerulonephritis, focal glomerular sclerosis, minimal change disease, cryoglobulinemia, Anti-Neutrophil Cytoplasmic Antibody (ANCA)-positive vasculitis, ANCA-negative vasculitis, amyloidosis, multiple myeloma, light chain deposition disease, complications of kidney transplant, chronic rejection of a kidney transplant, chronic allograft nephropathy, and the chronic effects of immunosuppressives. Preferably, chronic renal disease or chronic renal injury refers to chronic renal failure or chronic glomerulonephritis.

(x) "Predetermined level" refers generally to an assay cut-off value that is used to assess diagnostic/prognostic/therapeutic (or prophylactic) efficacy results by comparing the assay results against the predetermined level, where the predetermined level already has been linked or associated with various clinical parameters (e.g., severity of disease, progression/nonprogression/improvement, etc.). While the present disclosure may provide exemplary predetermined levels, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined level (cutoff) may vary between assays, the correlations as described herein should be generally applicable.

(y) "Risk" refers to the possibility or probability of a particular event occurring either presently, or, at some point in the future. "Risk stratification" refers to an array of known clinical risk factors that allows physicians to classify patients into a low, moderate, high or highest risk of developing a particular disease, disorder or condition.

(z) "About" refers to approximately a +/−10% variation from the stated value. It is to be understood that such a variation is always included in any given value provided herein, whether or not specific reference is made to it.

(aa) "Modulate" is used herein to refer to any change in the expression (such as up-regulation or down-regulation) or activity (such as stimulation or inhibition) of a protein isoform (or a variant thereof, a fragment thereof, or a fragment of a variant thereof). Modulation of expression or activity can be determined in accordance with routine assays known in the art.

(ab) "Enriched" means that the amount of a particular component, such as a protein (in the context of this disclosure, for example, NGAL), has been increased relative to the amount of other protein and non-protein components in a given composition.

(ac) "Two-dimensional electrophoresis" (2DE) is a technique comprising isoelectric focusing followed by denaturing electrophoresis. A two-dimensional gel (2D-gel) containing a plurality of separated proteins (e.g., isoforms of NGAL), which are separated according to their electrophoretic mobility and pI, is generated. Preferably, polyacrylamide and sodium dodecyl sulfate (SDS) are used during denaturing electrophoresis. A computer-generated digital profile of the array is generated, representing the identity, apparent molecular weight, pI, and relative abundance of the plurality of separated proteins, thereby enabling computer-mediated comparisons of profiles from multiple samples, as well as computer-aided excision of separated proteins of interest (e.g., isoforms of NGAL).

(ad) A "feature" refers to a spot detected in a 2D-gel. "Feature associated with a protein isoform," more specifically "feature associated with an NGAL isoform," refers to a feature that is differentially present in a sample (e.g., a sample of urine) from a subject having a condition, disease or disorder as compared to a sample from a subject that does not have the same condition, disease or disorder. A feature is "differentially present" in one sample as compared to another sample when a method for detecting the feature or NGAL isoform provides a different signal when applied to one sample as opposed to the other sample. A feature or isoform is increased in one sample as compared to the other sample if it is more abundant in the former or if it is detectable in the former but not in the latter. A feature or isoform is decreased in one sample as compared to the other sample if it is less abundant in the former or if it is undetectable in the former but detectable in the latter. The relative abundance of a feature in two or more samples is determined by reference to a normalized signal (i.e., by reference to the total protein in the sample being analyzed (e.g., the total protein loaded onto the gel or the total signal detected as the sum of all proteins in the sample) and by comparison of the normalized signal for the feature in one sample or sample set with the normalized signal for the same feature in another sample or sample set so as to identify features that are "differentially present" in one sample with respect to the other sample.

(ae) "Identical" or "identity," as used herein in the context of two or more polypeptide or polynucleotide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation.

(af) "Substantially identical" as used herein may mean that a first sequence and a second sequence are at least from about 50% to about 99% identical over a region of from about 8 to about 100 or more residues (including, in particular, any range within from about 8 to about 100 residues).

(ag) "Variant" as used herein may mean a peptide or polypeptide that differs in amino acid sequence by the insertion, deletion, or conservative substitution of amino acids, but retains at least one biological activity. For purposes of this disclosure, "biological activity" includes the ability to be bound by a specific antibody. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art (Kyte et al., J. Mol. Biol. 157:105-132 (1982)). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (U.S. Pat. No. 4,554,101, which is incorporated herein by reference). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Variant may also refer to a protein that is (i) a portion of a referenced protein, which may be from about 8 to about 100 or more amino acids (including, in particular, any range within from about 8 to about 100 residues); or (ii) a protein that is substantially identical to a referenced protein. A variant may also be a differentially processed protein, such as by proteolysis, phosphorylation, or other post-translational modification.

(ah) "Chinese Hamster Ovary (or CHO) cells that recombinantly produce NGAL" as used herein include in one aspect, a CHO cell line which produces glycosylated mutant human NGAL. Preferably, the glycosylated mutant human NGAL comprises an amino acid substitution at the amino acid corresponding to amino acid 87 of the amino acid sequence of wild-type human NGAL (e.g., SEQ ID NO:1). More preferably, the amino acid substitution is the replacement of a cysteine with a serine (See, e.g., SEQ ID NO:4, 5 or 6). Most preferably, the CHO cell line is a CHO cell line that has been deposited with the American Type Culture Collection (ATCC) at 10801 University Boulevard, Manassas, Va. 20110-2209 on Jan. 23, 2007 and received ATCC Accession No. PTA-8168. The CHO cell line having ATCC Accession No. PTA-8168 (CHO cell clone #734, also known as "mutant C87S NGAL rAg CHO 734" and "mutant NGAL rAg CHO C87S cell line") produces a glycosylated mutant human NGAL comprising an amino acid sequence of SEQ ID NO:5 or 6. The cell line further is described in U.S. Provisional Application No. 60/981,470 filed on Oct. 19, 2007, and U.S. patent application Ser. No. 12/104,408 filed on Apr. 16, 2008, both of which are incorporated by reference in their entireties for their teachings regarding same.

The terminology used herein is for the purpose of describing particular embodiments only and is not otherwise intended to be limiting.

Enriched Compositions Comprising NGAL Isoforms

A composition comprising enriched NGAL is provided. The NGAL has a molecular weight of about 24.9 kilodaltons (kDa) to about 25.9 kDa. The composition comprises a plurality of isoforms of NGAL having isoelectric points (pIs) ranging from about 5.9 to about 9.1. Desirably, the composition is obtained by enrichment methods. Purification methods can lead to selective loss of isoforms, particularly if charge-separation is employed. For example, attempts to purify NGAL based on the predicted pI for the native polypeptide, i.e., pI=9.02, can lead to loss of isoforms of NGAL having lower pIs. Preferably, the composition comprises at least about five isoforms of NGAL. The at least about five isoforms of NGAL comprise an isoform having a pI of about 5.9, an isoform having a pI of about 6.7, an isoform having a pI of about 8.3, an isoform having a pI of about 8.8, and an isoform having a pI of about 9.1. Preferably, the composition is enriched from urine.

Another composition comprising enriched NGAL is provided. The NGAL has a molecular weight of about 25.9 kDa to about 27.9 kDa. The composition comprises a plurality of isoforms of NGAL having pIs ranging from about 5.6 to about 9.1. Desirably, the composition is obtained by enrichment methods. Preferably, the composition comprises at least about seven isoforms of NGAL. The at least about seven isoforms of NGAL comprise an isoform having a pI of about 5.6, an isoform having a pI of about 5.9, an isoform having a pI of about 6.3, an isoform having a pI of about 6.5, an isoform having a pI of about 6.8, an isoform having a pI of about 7.5, and an isoform having a pI of about 9.1. Preferably, the composition is enriched from a composition, which was obtained from Chinese hamster ovary (CHO) cells that recombinantly produce NGAL, by acidification, extraction with ethanol and zinc acetate, and, in the absence of separation of molecules based on charge, ultra-filtration buffer exchange, size-exclusion chromatography, and/or ammonium sulfate precipitation.

Method of Enriching Compositions Comprising NGAL Isoforms

A method of obtaining from urine a composition comprising a plurality of isoforms of NGAL is provided. The sample of urine can be provided in any suitable tube, container, bag, etc. Such means of collection can be made with any suitable material known in the art (e.g., plastic or glass, which can be siliconized), including a suitable plastic material that is non-reactive and does not interfere with the test sample. Preferred plastic materials include any type of polyethylene terepththlate (PET) or polypropylene. Various types of means of collection are commercially available.

The method comprises enriching NGAL in urine without separating molecules based on charge. Optionally, any particulate matter, such as cells (e.g., red blood cells, white blood cells, and epithelial cells), bacteria, urine casts (e.g., epithelial cell casts of renal tubules, red blood cell casts, white blood cell casts, hyaline or mucoprotein casts, granular casts, waxy casts, and fatty casts), and urine crystals (e.g., calcium oxalate crystals, triple phosphate crystals, uric acid crystals, and cysteine crystals), is removed prior to enriching NGAL. Particulate matter can be removed by centrifugation. Alternatively, the method comprises enriching NGAL in a composition, which was obtained from CHO cells that recombinantly produce NGAL.

While any suitable method that does not involve charge separation can be used, a preferred method is as exemplified herein. Briefly, after centrifugation of the urine or the composition obtained from recombinant CHO cells, the supernatant is acidified, e.g., to a pH below about 7.0, such as below about 6.0, below about 5.0, or below about 4.0. Preferably, the supernatant is acidified to a pH of about 3.0, such as from about 2.9 to about 3.1. After the supernatant is acidified, ethanol is added to the supernatant and thoroughly mixed with the supernatant. Afterwards, the mixture is centrifuged, and zinc acetate is added to the supernatant and thoroughly mixed with the supernatant. Afterwards, the mixture is centrifuged. The pellet is then resuspended and enriched for NGAL by any suitable method, which includes, but is not limited to, ultra-filtration buffer exchange, size-exclusion chromatography, and/or ammonium sulfate precipitation.

Method of Analyzing Compositions Comprising Enriched NGAL

A composition comprising enriched NGAL can be analyzed by any suitable method, such as two-dimensional electrophoresis (2DE). 2DE enables determination of the charge (isoelectric point, pI) and size (molecular weight, MW) properties of NGAL-active protein isoforms, such as by correlation of migration in both dimensions to internal calibration standards. NGAL-active protein amongst all spots in 2DE is identified by Western blot using monoclonal and/or polyclonal antibodies raised against purified NGAL protein, such as recombinant human NGAL protein.

Accordingly, also provided is a method of analyzing NGAL isoforms enriched from urine or a composition, which was obtained from recombinant CHO cells. The method comprises analyzing the urine or the composition by 2DE and Western blot. Preferably, NGAL was enriched in the urine or the composition obtained from recombinant CHO cells without separating molecules based on charge. Also, preferably, any particulate matter in the urine or the composition obtained from recombinant CHO cells was removed. Preferably, the urine or the composition obtained from recombinant CHO cells was acidified and then extracted with ethanol and zinc acetate. Afterwards, the urine or the composition obtained from recombinant CHO cells was preferably subjected to ultra-filtration buffer exchange, size-exclusion chromatography, and/or ammonium sulfate precipitation.

Isoforms of NGAL also can be characterized by mass-to-charge ratio as determined by mass spectrometry, by the shape of their spectral peak in time-of-flight mass spectrometry, and by their binding characteristics to adsorbent surfaces. Such characteristics enable one of ordinary skill in the art to determine whether a particular isoform of NGAL is associated with a condition, disease or disorder endpoint without knowing the amino acid sequence of the isoform. For example, samples of urine from subjects having a particular condition, disease or disorder, e.g., renal disease, and samples of urine from subjects not having the particular condition, disease or disorder, e.g., renal disease, can be enriched for NGAL and applied to SELDI (surface-enhanced laser desorption/ionization) biochips and spectra of NGAL isoforms present in the sample can be generated by time-of-flight mass spectrometry. The spectra can be analyzed using appropriate software. By comparing the spectra between the two groups of subjects, it can be determined if the presence, amount or concentration of one or more isoforms of NGAL is/are characteristic of the group having a particular condition, disease or disorder, such as renal disease. Once a correlation has been established between one or more isoforms of NGAL and a particular condition, disease or disorder, the one or more isoforms can be used in any of the methods described herein for assessing the particular condition, disease or disorder, whether by affinity capture and mass spectrometry, immunoassay directed against the one or more isoforms, or other such methods. Of course, other methods known to one skilled in the art also can be employed.

An isoform of NGAL associated with a particular condition, disease or disorder endpoint can be isolated and sequenced. For example, the isoform can be isolated by any suitable method, such as by gel electrophoresis, in which case the band in the gel corresponding to the isoform is cut out of the gel, and the protein is digested with a protease, such as trypsin or V8 protease. The molecular weights of the digestion fragments can be used to search databases for sequences that match the molecular weights of the digestion fragments generated by the various enzymes. Alternatively, the digestion fragments can be separated by mass spectrometry and further fragmented by collision-induced cooling, in which case a polypeptide ladder is generated and analyzed by mass spectrometry (i.e., "tandem mass spectrometry" or "tandem MS"). Amino acids are identified by the differences in mass of the members of the polypeptide ladders.

Any unique epitopes on the isoform, i.e., epitopes that distinguish that particular isoform from other isoforms of NGAL, can be used to generate monoclonal antibodies, each of which specifically binds to that particular isoform of NGAL of interest. In the event that more than one isoform of NGAL is of interest, monoclonal antibodies, which specifically bind to such isoforms, can be used in conjunction in accordance with the methods described herein (e.g., diagnosis, prognosis, and assessment of efficacy of prophylactic/therapeutic treatment). Such isoforms and/or monoclonal antibodies thereto also can be used in drug development (see, e.g., U.S. Pat. App. Pub. No. 2007/0166765, which is incorporated by reference in its entirety for its teachings regarding protein isoforms).

Synthetic Production

Once sequenced, polypeptides, such as one or more isoforms of NGAL (or a fragment thereof, a variant thereof, or a fragment of a variant thereof) or one or more mAbs (or a fragment thereof), each of which specifically binds to a particular isoform of NGAL, can be synthesized using methods known in the art, such as, for example, exclusive solid phase synthesis, partial solid phase synthesis, fragment condensation, and classical solution synthesis. See, e.g., Merrifield, J. Am. Chem. Soc. 85: 2149 (1963). On solid phase, the synthesis typically begins from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the tradename BIO-BEADS SX-1 by Bio Rad Laboratories (Richmond, Calif.), and the preparation of the hydroxymethyl resin is described by Bodonszky et al., Chem. Ind. (London) 38: 1597 (1966). The benzhydrylamine (BHA) resin has been described by Pietta and Marshall, Chem. Comm. 650 (1970) and is commercially available from Beckman Instruments, Inc. (Palo Alto, Calif.) in the hydrochloride form. Automated peptide synthesizers are commercially available, as are services that make peptides to order.

Thus, the polypeptides can be prepared by coupling an alpha-amino protected amino acid to the chloromethylated resin with the aid of, for example, cesium bicarbonate catalyst, according to the method described by Gisin, Hely. Chim. Acta. 56: 1467 (1973). After the initial coupling, the alpha-amino protecting group is removed by a choice of reagents including trifluoroacetic acid (TFA) or hydrochloric acid (HCl) solutions in organic solvents at room temperature.

Suitable alpha-amino protecting groups include those known to be useful in the art of stepwise synthesis of peptides. Examples of alpha-amino protecting groups are: acyl type protecting groups (e.g., formyl, trifluoroacetyl, and acetyl), aromatic urethane type protecting groups (e.g., benzyloxycarbonyl (Cbz) and substituted Cbz), aliphatic urethane protecting groups (e.g., t-butyloxycarbonyl (Boc), isopropyloxycarbonyl, and cyclohexyloxycarbonyl), and alkyl type protecting groups (e.g., benzyl and triphenylmethyl). Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride and dimethyl formamide (DMF) mixtures.

After the desired amino acid sequence has been completed, the desired peptide is decoupled from the resin support by treatment with a reagent, such as trifluoroacetic acid or hydrogen fluoride (HF), which not only cleaves the peptide from the resin, but also cleaves all remaining side chain protecting groups. When the chloromethylated resin is used, HF treatment results in the formation of the free peptide acids. When the benzhydrylamine resin is used, HF treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These and other solid phase peptide synthesis procedures are well-known in the art. Such procedures are also by Stewart and Young in *Solid Phase Peptide Syntheses* (2nd Ed., Pierce Chemical Company, 1984).

Recombinant Production

A polynucleotide sequence encoding a polypeptide/protein form of interest, such as an isoform of NGAL (or a fragment thereof, a variant thereof, or a fragment of a variant thereof) or a monoclonal antibody, which specifically binds to a particular isoform of NGAL, can be prepared using an oligonucleotide synthesizer. Oligonucleotides are designed based on the amino acid sequence of the polypeptide/protein (full-length, a fragment thereof, a variant thereof, or a fragment of a variant thereof). Preferably, codons, which are favored in the host cell in which the recombinant protein/polypeptide form of interest will be produced, are selected. For example, several small oligonucleotides coding for portions of the desired polypeptide/protein form of interest can be synthesized and assembled by polymerase chain reaction (PCR), ligation, or ligation chain reaction (LCR). The individual oligonucleotides typically contain 5' or 3' overhangs for complementary assembly.

Once assembled (such as by synthesis, site-directed mutagenesis or another method), the polynucleotide sequence encoding the polypeptide/protein form of interest can be inserted into a recombinant vector and operably linked to any control sequences necessary for expression thereof in the desired transformed host cell.

Although not all vectors and expression control sequences may function equally well to express a polynucleotide sequence of interest and not all hosts function equally well with the same expression system, it is believed that those skilled in the art will be able to make easily a selection among vectors, expression control sequences, optimized codons, and hosts for use in the present disclosure without any undue experimentation. For example, in selecting a vector, the host must be considered because the vector must be able to replicate in it or be able to integrate into the chromosome. The vector's copy number, the ability to control that copy number, and the expression of any other proteins encoded by the vector, such as antibiotic markers, also should be considered. In selecting an expression control sequence, a variety of factors also can be considered. These include, but are not limited to, the relative strength of the sequence, its controllability, and its compatibility with the polynucleotide sequence encoding the polypeptide/protein form of interest, particularly as regards potential secondary structures. Hosts should be selected by consideration of their compatibility with the chosen vector, their codon usage, their secretion characteristics, their ability to fold the polypeptide correctly, their fermentation or culture requirements, their ability (or lack thereof) to glycosylate the protein, and the ease of purification of the products coded for by the nucleotide sequence, etc.

The recombinant vector may be an autonomously replicating vector, namely, a vector existing as an extrachromosomal entity, the replication of which is independent of chromosomal replication (such as a plasmid). Alternatively, the vector can be one which, when introduced into a host cell, is integrated into the host cell genome and replicated together with the chromosome(s) into which it has been integrated.

The vector is preferably an expression vector, in which the polynucleotide sequence encoding the polypeptide/protein form of interest is operably linked to additional segments required for transcription of the polynucleotide sequence. The vector is typically derived from plasmid or viral DNA. A number of suitable expression vectors for expression in the host cells mentioned herein are commercially available or described in the literature. Useful expression vectors for eukaryotic hosts, include, but are not limited to, vectors comprising expression control sequences from SV40, bovine papilloma virus, adenovirus and cytomegalovirus. Specific vectors include, pcDNA3.1 (+)\Hyg (Invitrogen Corp., Carlsbad, Calif.) and pCI-neo (Stratagene, La Jolla, Calif.). Examples of expression vectors for use in yeast cells include, but are not limited to, the 2µ plasmid and derivatives thereof, the POT1 vector (See, U.S. Pat. No. 4,931,373), the pJSO37 vector (described in Okkels, Ann. New York Acad. Sci. 782: 202-207 (1996)) and pPICZ A, B or C (Invitrogen Corp.). Examples of expression vectors for use in insect cells include, but are not limited to, pVL941, pBG311 (Cate et al., Cell 45: 685-698 (1986)), pBluebac 4.5 and pMelbac (both of which are available from Invitrogen Corp.). A preferred vector for use in the invention is pJV (available from Abbott Laboratories, Abbott Bioresearch Center, Worcester, Mass.).

Other vectors that can be used allow the polynucleotide sequence encoding the polypeptide/protein form of interest to be amplified in copy number. Such amplifiable vectors are well-known in the art. These vectors include, but are not limited to, those vectors that can be amplified by dihydrofolate reductase (DHFR) amplification (see, for example, Kaufman, U.S. Pat. No. 4,470,461; and Kaufman et al., Mol. Cell. Biol. 2: 1304-1319 (1982)) and glutamine synthetase (GS) amplification (see, for example, U.S. Pat. No. 5,122,464 and European Pat. App. Pub. No. 0 338 841).

The recombinant vector may further comprise a DNA sequence enabling the vector to replicate in the host cell in question. An example of such a sequence (when the host cell is a mammalian cell) is the SV40 origin of replication. When the host cell is a yeast cell, suitable sequences enabling the vector to replicate are the yeast plasmid 2µ replication genes REP 1-3 and origin of replication.

The vector may also comprise a selectable marker, namely, a gene or polynucleotide, the product of which complements a defect in the host cell, such as the gene coding for DHFR or the *Schizosaccharomyces pombe* TPI gene (see Russell, Gene 40: 125-130 (1985)), or one that confers resistance to a drug, such as ampicillin, kanamycin, tetracycline, chloramphenicol, neomycin, hygromycin or methotrexate. For filamentous fungi, selectable markers include, but are not limited to, amdS, pyrG, arcB, niaD and sC.

As used herein, the phrase "control sequences" refers to any components, which are necessary or advantageous for the expression of a polypeptide/protein form of interest. Each control sequence may be native or foreign to the nucleic acid sequence encoding the polypeptide/protein form of interest. Such control sequences include, but are not limited to, a leader, a polyadenylation sequence, a propeptide sequence, a promoter, an enhancer or an upstream activating sequence, a signal peptide sequence and a transcription terminator. At a minimum, the control sequences include at least one promoter operably linked to the polynucleotide sequence encoding the polypeptide/protein form of interest.

As used herein, the phrase "operably linked" refers to the covalent joining of two or more polynucleotide sequences, by means of enzymatic ligation or otherwise, in a configuration relative to one another such that the normal function of the sequences can be performed. For example, a polynucleotide sequence encoding a presequence or secretory leader is operably linked to a polynucleotide sequence for a polypeptide if it is expressed as a preprotein that participates in the secretion of the polypeptide; a promoter or enhancer is operably linked to a coding sequence if it affects the transcription of the sequence; a ribosome binding site is operably linked to a coding sequence if it is positioned so as to facilitate translation. Generally, "operably linked" means that the polynucleotide sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

A wide variety of expression control sequences may be used in the present disclosure. Such useful expression control sequences include the expression control sequences associated with structural genes of the foregoing expression vectors as well as any sequence known to control the expression of genes of prokaryotic or eukaryotic cells or their viruses, and various combinations thereof. Examples of suitable control sequences for directing transcription in mammalian cells include the early and late promoters of SV40 and adenovirus, for example, the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus E1b region polyadenylation signals, and the Kozak consensus sequence (Kozak, J. Mol. Biol. 196: 947-50 (1987)).

In order to improve expression in mammalian cells a synthetic intron may be inserted in the 5' untranslated region of the polynucleotide sequence encoding the polypeptide/protein form of interest. An example of a synthetic intron is the synthetic intron from the plasmid pCI-Neo (available from Promega Corporation, Madison, Wis.).

Examples of suitable control sequences for directing transcription in insect cells include, but are not limited to, the polyhedrin promoter, the P10 promoter, the baculovirus immediate early gene 1 promoter and the baculovirus 39K delayed-early gene promoter and the SV40 polyadenylation sequence.

Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4-c promoter and the inducible GAL promoter.

Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulas* glucoamylase, *A. nidulans* acetamidase, *Rhizomucor miehei* aspartic proteinase or lipase, the TPI1 terminator and the ADH3 terminator.

The polynucleotide sequence encoding the polypeptide/protein form of interest may or may not also include a polynucleotide sequence that encodes a signal peptide. The signal peptide is present when the polypeptide/protein form of interest is to be secreted from the cells in which it is expressed. Such signal peptide, if present, should be one recognized by the cell chosen for expression of the polypeptide. The signal peptide may be homologous (for example, it may be that normally associated with the polypeptide/protein form of interest) or heterologous (namely, originating from another source than the polypeptide/protein form of interest) to the polypeptide/protein form of interest or may be homologous or heterologous to the host cell, namely, be a signal peptide normally expressed from the host cell or one which is not normally expressed from the host cell. Accordingly, the signal peptide may be prokaryotic, for example, derived from a bacterium, or eukaryotic, for example, derived from a mammalian, insect, filamentous fungal, or yeast cell.

The presence or absence of a signal peptide will, for example, depend on the expression host cell used for the production of the polypeptide/protein form of interest. For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. For use in insect cells, the signal peptide may be derived from an insect gene (see, Int'l Pat. App. Pub. No. WO 90/05783), such as the lepidopteran *Manduca sexta* adipokinetic hormone precursor, (see, U.S. Pat. No. 5,023,328), the honeybee melittin (Invitrogen), ecdysteroid UDP glucosyltransferase (egt) (Murphy et al., Protein Expression and Purification 4: 349-357 (1993)), or human pancreatic lipase (hpl) (Methods in Enzymology 284: 262-272 (1997)).

Specific examples of signal peptides for use in mammalian cells include murine Ig kappa light chain signal peptide (Coloma, J. Imm. Methods 152: 89-104 (1992)). For use in yeast cells suitable signal peptides include the α-factor signal peptide from *S. cerevisiae* (see U.S. Pat. No. 4,870,008), the signal peptide of mouse salivary amylase (see Hagenbuchle et al., Nature 289: 643-646 (1981)), a modified carboxypeptidase signal peptide (see Valls et al., Cell 48: 887-897 (1987)), the yeast BAR1 signal peptide (see Int'l Pat. App. Pub. No. WO 87/02670), and the yeast aspartic protease 3 (YAP3) signal peptide (see Egel-Mitani et al., Yeast 6: 127-137 (1990)).

Any suitable host may be used to produce the polypeptide/protein form of interest (e.g., full-length, fragment, variant, or fragment of a variant) of the present disclosure, including bacteria, fungi (including yeasts), plant, insect mammal or other appropriate animal cells or cell lines, as well as transgenic animals or plants. When a non-glycosylating organism, such as *E. coli*, is used to express a glycosylated polypeptide/protein form of interest, the expression is preferably followed by suitable in vitro glycosylation in order to produce the glycosylated polypeptide/protein form of interest.

Examples of bacterial host cells include, but are not limited to, gram-positive bacteria such as strains of *Bacillus*, for example, *B. brevis* or *B. subtilis*, *Pseudomonas* or *Streptomyces*, or gram-negative bacteria, such as strains of *E. coli*. The introduction of a vector into a bacterial host cell may, for instance, be effected by protoplast transformation (see, for example, Chang et al., Molecular General Genetics 168: 111-115 (1979)), using competent cells (see, for example, Young et al., J. of Bacteriology 81: 823-829 (1961)), or Dubnau et al., J. Molec. Biol. 56: 209-221 (1971)), electroporation (see, for example, Shigekawa et al., Biotechniques 6: 742-751 (1988)), or conjugation (see, for example, Koehler et al., J. of Bacteriology 169: 5771-5278 (1987)).

Examples of suitable filamentous fungal host cells include, but are not limited to, strains of *Aspergillus*, for example, *A. oryzae, A. niger*, or *A. nidulans, Fusarium* or *Trichoderma*. Fungal cells may be transformed by a process involving protoplast formation, transformation of the protoplasts, and regeneration of the cell wall using techniques known to those skilled in the art. Suitable procedures for transformation of *Aspergillus* host cells are described in European Pat. App. 0 238 023 and U.S. Pat. No. 5,679,543. Suitable methods for transforming *Fusarium* species are described by Malardier et al., Gene 78: 147-156 (1989) and Int'l Pat. App. Pub. No. WO 96/00787. Yeast may be transformed using the procedures described by Becker and Guarente, In Abelson and Simon, editors, *Guide to Yeast Genetics and Molecular Biology, Methods in Enzymology* 194: 182-187, Academic Press, Inc., New York; Ito et al., J. of Bacteriology 153: 163 (1983); and Hinnen et al., PNAS USA 75: 1920 (1978).

Preferably, the glycosylated polypeptide/protein form of interest is glycosylated in vivo in a host cell that can generate the desired glycosylation. Thus, the host cell may be selected from a yeast cell, insect cell, or mammalian cell.

Examples of suitable yeast host cells include strains of *Saccharomyces*, for example, *S. cerevisiae, Schizosaccharomyces, Klyveromyces, Pichia*, such as *P. pastoris* or *P. methanolica*, and *Hansenula*, such as *H. polymorpha* or *yarrowia*. Methods for transforming yeast cells with heterologous polynucleotides and producing heterologous polypeptides therefrom are disclosed by Clontech Laboratories, Inc, Palo Alto, Calif. (in the product protocol for the Yeastmaker™ Yeast Tranformation System Kit), and by Reeves et al., FEMS Microbiol. Letters 99: 193-198 (1992), Manivasakam et al., Nucleic Acids Research 21: 4414-4415 (1993), and Ganeva et al., FEMS Microbiol. Letters 121: 159-164 (1994).

Examples of suitable insect host cells include, but are not limited to, a *Lepidoptora* cell line, such as *Spodoptera frugiperda* (Sf9 or Sf21) or *Trichoplusia ni* cells (High Five) (see, U.S. Pat. No. 5,077,214). Transformation of insect cells and production of heterologous polypeptides are well-known to those skilled in the art.

Examples of suitable mammalian host cells include Chinese hamster ovary (CHO) cell lines, Green Monkey cell lines (COS), mouse cells (for example, NS/O), Baby Hamster Kidney (BHK) cell lines, human cells (such as, human embryonic kidney cells (for example, HEK 293 (American Type Culture Collection (ATCC) Accession No. CRL-1573, ATCC, Manassas, Va.)) and plant cells in tissue culture. Preferably, the mammalian host cells are CHO cell lines and HEK 293 cell lines. Another preferred host cell is the B3.2 cell line (e.g., Abbott Laboratories, Abbott Bioresearch Center), or another DHFR-deficient (DHFR⁻) CHO cell line (e.g., available from Invitrogen).

Methods for introducing exogenous polynucleotides into mammalian host cells include calcium phosphate-mediated transfection, electroporation, DEAE-dextran mediated transfection, liposome-mediated transfection, viral vectors and the transfection method described by Life Technologies Ltd., Paisley, UK, using Lipofectamine™ 2000. These methods are well-known in the art and are described, for example, by Ausbel et al. (eds.) *Current Protocols in Molecular Biology*, John Wiley & Sons, New York (1996). The cultivation of mammalian cells are conducted according to established methods, e.g., as disclosed in Jenkins, Ed., *Animal Cell Biotechnology, Methods and Protocols*, Human Press Inc., Totowa, N.J. (1999); and Harrison and Rae, *General Techniques of Cell Culture*, Cambridge University Press (1997).

In the production methods, cells are cultivated in a nutrient medium suitable for production of the polypeptide/protein form of interest using methods known in the art. For example, cells are cultivated by shake flask cultivation, small-scale or large-scale fermentation (including continuous, batch, fed-batch, or solid state fermentations) in laboratory or industrial fermenters performed in a suitable medium and under conditions allowing the glycosylated polypeptide/protein form of interest to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the ATCC). If a glycosylated polypeptide/protein form of interest is secreted into the nutrient medium, the polypeptide/protein form of interest can be recovered directly from the medium. If the polypeptide/protein form of interest is not secreted, it can be recovered from cell lysates.

The resulting polypeptide/protein form of interest may be recovered by methods known in the art. For example, the antipolypeptide/protein form of interest may be recovered from the nutrient medium by conventional procedures including, but not limited to, centrifugation, filtration, extraction, spray drying, evaporation, or precipitation.

The polypeptide/protein form of interest may be purified by a variety of procedures known in the art including, but not limited to, chromatography (such as, but not limited to, ion exchange, affinity, hydrophobic, chromatofocusing, and size exclusion), electrophoretic procedures (such as, but not limited to, preparative isoelectric focusing), differential solubility (such as, but not limited to, ammonium sulfate precipitation), SDS-PAGE, or extraction (see, for example, Janson and Ryden, editors, *Protein Purification*, VCH Publishers, New York (1989)).

A glycosylated polypeptide/protein form of interest can be optionally deglycosylated using routine techniques in the art. N-linked, O-linked or both N-linked and O-linked deglycosylations can be performed using routine techniques known in the art, such as by treating such polypeptides/proteins with one or more enzymes.

Examples of enzymes that can be used for deglycosylation include PNGase F for N-linked deglycosylation (Asn), and O-Glycanase for removing carbohydrates from O-linked sites (Ser and Thr). Other enzymes also can be used, such as Sialidase, β(1-4)-Galactosidase, and β-N-acetyl-Glucosaminidase, which cleave carbohydrates from special linkages. These enzymes and others are available from, e.g., Prozyme (San Leandro, Calif.) and Sigma-Aldrich (St. Louis, Mo.), and furthermore may be purchased in the form of mixtures or "cocktails." For example, the Sigma-Aldrich E-DE-GLY kit includes a cocktail of PNGase F, α-2(2,6,8,9) Neuraminidase, O-Glycosidase, β(1-4)-Galactosidase, and β-N-acetyl-Glucosaminidase, and the Enzymatic Deglycosylation Kit from Prozyme comprises PNGase F, O-Glycosidase, and Sialidase.

Cells for recombinant production include but are not limited to CHO cells that recombinantly produce NGAL, as further described herein. Also, in some instances, it might be desirable to use a CHO cell line which produces glycosylated human wild-type NGAL (namely, that which has the amino acid sequence of SEQ ID NO:1), wherein the CHO cell line has been deposited with American Type Culture Collection (ATCC) at 10801 University Boulevard, Manassas, Va. 20110-2209 on Nov. 21, 2006 and received ATCC Accession No. PTA-8020. Preferably, the wild-type human NGAL produced by the CHO cell line having ATCC Accession No. PTA-8020 (also known as "wild-type NGAL rAg CHO 662 cell line") has a molecular weight of about 25 kilodaltons (kDa). The cell line further is described in U.S. Provisional Application No. 60/981,470 filed on Oct. 19, 2007, and U.S. patent application Ser. No. 12/104,408 filed on Apr. 16, 2008, both of which are incorporated by reference in their entireties for their teachings regarding same.

Antibody Production

An antibody (or a fragment thereof) that specifically binds to a particular isoform of NGAL (or a fragment thereof) can be made using a variety of different techniques known in the art. For example, polyclonal and monoclonal antibodies can be raised by immunizing a suitable subject (such as, but not limited to, a rabbit, a goat, a mouse, or other mammal) with an immunogenic preparation, which contains a suitable immunogen. The immunogen can be enriched/purified and isolated from a cell that produces it using affinity chromatography, immune-precipitation or other techniques, which are well-known in the art. Alternatively, immunogen can be prepared using chemical synthesis using routine techniques known in the art (such as, but not limited to, a synthesizer). The antibodies raised in the subject can then be screened to determine if the antibodies bind to the immunogen (or a fragment thereof).

The unit dose of immunogen (namely, the purified protein, tumor cell expressing the protein, or recombinantly expressed immunogen (or a fragment or a variant (or a fragment thereof) thereof) and the immunization regimen will depend upon the subject to be immunized, its immune status, and the body weight of the subject. To enhance an immune response in the subject, an immunogen can be administered with an adjuvant, such as Freund's complete or incomplete adjuvant.

Immunization of a subject with an immunogen as described above induces a polyclonal antibody response. The antibody titer in the immunized subject can be monitored over time by standard techniques such as an ELISA using an immobilized antigen.

Other methods of raising antibodies include using transgenic mice, which express human immunoglobin genes (see, for example, Int'l Pat. App. Pub. Nos. WO 91/00906, WO 91/10741, and WO 92/03918). Alternatively, human monoclonal antibodies can be produced by introducing an antigen into immune-deficient mice that have been engrafted with human antibody-producing cells or tissues (for example, human bone marrow cells, peripheral blood lymphocytes (PBL), human fetal lymph node tissue, or hematopoietic stem cells). Such methods include raising antibodies in SCID-hu mice (see, for example, Int'l Pat. App. Pub. No. WO 93/05796; U.S. Pat. No. 5,411,749; or McCune et al., Science 241: 1632-1639 (1988)) or Rag-1/Rag-2 deficient mice. Human antibody-immune deficient mice are also commercially available. For example, Rag-2 deficient mice are available from Taconic Farms (Germantown, N.Y.).

Monoclonal antibodies can be generated by immunizing a subject with an immunogen. At the appropriate time after immunization, for example, when the antibody titers are at a sufficiently high level, antibody-producing cells can be harvested from an immunized animal and used to prepare monoclonal antibodies using standard techniques. For example, the antibody-producing cells can be fused by standard somatic cell fusion procedures with immortalizing cells, such as myeloma cells, to yield hybridoma cells. Such techniques are well-known in the art, and include, for example, the hybridoma technique as originally developed by Kohler and Milstein, Nature 256: 495-497 (1975)), the human B cell hybridoma technique (Kozbar et al., Immunology Today 4: 72 (1983)), and the Epstein-Barr virus (EBV)-hybridoma technique to produce human monoclonal antibodies (Cole et al., *Monoclonal Antibodies and Cancer Therapy*, Alan R. Liss, Inc. pp. 77-96 (1985)). The technology for producing monoclonal antibody hybridomas is well-known to those skilled in the art.

Monoclonal antibodies also can be made by harvesting antibody-producing cells, for example, splenocytes, from transgenic mice, which express human immunoglobulin genes and which have been immunized with the immunogen. The splenocytes can be immortalized through fusion with human myelomas or through transformation with EBV. These hybridomas can be made using human B cell- or EBV-hybridoma techniques described in the art (See, for example, Boyle et al., European Pat. Pub. No. 0 614 984).

Hybridoma cells producing a monoclonal antibody, which specifically binds to the immunogen, are detected by screening the hybridoma culture supernatants by, for example, screening to select antibodies that specifically bind to the immobilized immunogen (or fragment thereof), or by testing the antibodies as described herein to determine if the antibodies have the desired characteristics, namely, the ability to bind to immunogen (or fragment thereof). After hybridoma cells are identified that produce antibodies of the desired specificity, the clones may be subcloned, e.g., by limiting dilution procedures, for example the procedure described by Wands et al. (Gastroenterology 80: 225-232 (1981)), and grown by standard methods.

Hybridoma cells that produce monoclonal antibodies that test positive in the screening assays described herein can be cultured in a nutrient medium under conditions and for a time sufficient to allow the hybridoma cells to secrete the monoclonal antibodies into the culture medium, to thereby produce whole antibodies. Tissue culture techniques and culture media suitable for hybridoma cells are generally described in the art (See, for example, R. H. Kenneth, in *Monoclonal Antibodies: A New Dimension In Biological Analyses*, Plenum Publishing Corp., New York, N.Y. (1980)). Conditioned hybridoma culture supernatant containing the antibody can then be collected. The monoclonal antibodies secreted by the subclones optionally can be isolated from the culture medium by conventional immunoglobulin purification procedures such as, for example, protein A chromatography, hydroxylapatite chromatography, gel electrophoresis, dialysis, or affinity chromatography.

Monoclonal antibodies can be engineered by constructing a recombinant combinatorial immunoglobulin library and screening the library with the immunogen or a fragment thereof. Kits for generating and screening phage display libraries are commercially available (See, for example, the Pharmacia Recombinant Phage Antibody System, Catalog No. 27-9400-01; and the Stratagene SurfZAP Phage Display Kit, Catalog No. 240612). Likewise, yeast display vectors are known in the art and are commercially available (for example, pYD1 available from Invitrogen). Briefly, the antibody library is screened to identify and isolate phages or yeast cells that express an antibody that specifically binds to the immunogen or a fragment thereof. Preferably, the primary screening of the library involves screening with an immobilized immunogen or a fragment thereof.

Following screening, the display phage or yeast is isolated and the polynucleotide encoding the selected antibody can be recovered from the display phage or yeast (for example, from the phage or yeast genome) and subcloned into other expression vectors (e.g., into *Saccharomyces cerevesiae* cells, for example EBY100 cells (Invitrogen)) by well-known recombinant DNA techniques. The polynucleotide can be further manipulated (for example, linked to nucleic acid encoding additional immunoglobulin domains, such as additional constant regions) and/or expressed in a host cell.

Furthermore, in some aspects of the disclosure, it may be possible to employ commercially available anti-NGAL antibodies or methods for production of anti-NGAL antibodies as described in the literature. These include, but are not limited to, those available from Santa Cruz Biotechnology, Inc. (Santa Cruz, Calif.) and R&D Systems (Minneapolis, Minn.).

Once a monoclonal antibody that specifically binds to a particular isoform of NGAL is obtained in accordance with methods described above, it can be sequenced in accordance with methods known in the art and then made using recombinant DNA technology, chemical synthesis, or a combination of chemical synthesis and recombinant DNA technology. Specifically, an isolated nucleic acid comprising a nucleotide sequence encoding the antibody can be synthesized. An oligonucleotide synthesizer can be used. One of ordinary skill in the art will readily appreciate that, due to the degeneracy of the genetic code, more than one nucleotide sequence can encode a given amino acid sequence. In this regard, a nucleotide sequence encoding a substantially identical amino acid sequence can be used, provided that the variant antibody as expressed competes with the original antibody. Codons, which are favored by a given host cell, preferably are selected for recombinant production. Nucleotide sequences can be combined with other nucleotide sequences using PCR, ligation, or LCR to encode an anti-NGAL antibody or an antigenically reactive fragment thereof. The individual oligonucleotides typically contain 5' or 3' overhangs for complementary assembly. Once assembled, the nucleotide sequence encoding an anti-NGAL antibody or antigenically reactive fragment thereof can be inserted into a vector, operably linked to control sequences as necessary for expression in a given host cell, and introduced (such as by transformation or transfection) into a host cell. The nucleotide sequence can be further manipulated (for example, linked to nucleic acid encoding additional immunoglobulin domains, such as additional constant regions) and/or expressed in a host cell.

Fragments of anti-NGAL antibodies (and variants thereof) also can be used in the context of the present disclosure. For example, the antibody fragment can include, but is not limited to, a Fab, a Fab', a Fab'-SH fragment, a disulfide linked Fv, a single chain Fv (scFv) and a F(ab')$_2$ fragment. Various techniques are known to those skilled in the art for the production of antibody fragments. Such fragments can be derived via proteolytic digestion of intact antibodies (see, for example, Morimoto et al., J. Biochem. Biophys. Methods 24: 107-117 (1992); and Brennan et al., Science 229: 81 (1985)). For example, Fab fragments can be prepared from whole antibodies by papain digestion, whereas F(ab')$_2$ fragments can be prepared from whole antibodies by pepsin digestion. Such fragments also can be produced directly by recombinant host cells. For example, Fab'-SH fragments can be directly recovered from *E. coli* and chemically coupled to form F(ab')$_2$ fragments (see, e.g., Carter et al., Bio/Technology 10: 163-167 (1992)). In another embodiment, the F(ab')$_2$ is formed using the leucine zipper GCN4 to promote assembly of the F(ab')$_2$ molecule. Alternatively, Fv, Fab or F(ab')$_2$ fragments can be isolated directly from recombinant host cell culture. Single chain variable region fragments (scFv) are made by linking light and/or heavy chain variable regions by using a short linking peptide or sequence (see, e.g., Bird et al., Science 242: 423-426 (1998)). The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art. Moreover, other forms of single chain antibodies, such as diabodies are also contemplated by the present disclosure. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., PNAS USA 90: 6444-6448 (1993); and Poljak et al., Structure 2: 1121-1123 (1994)).

The antibody and antigenically reactive fragment thereof have a variety of uses. In one aspect, the antibody (or fragment thereof) can be used as one or more immunodiagnostic reagents. For example, the antibodies of the present disclosure can be used as one or more immunodiagnostic reagents in one or more methods for detecting the presence, amount or concentration of NGAL in a test sample. More specifically, an antibody (or an antigenically reactive fragment thereof) that specifically binds to a particular isoform of NGAL can be used to capture any of that isoform that may be present in a test sample. A detectably labeled anti-NGAL antibody, a detectably labeled fragment of an anti-NGAL antibody that can bind to the NGAL isoform, or a detectably labeled variant (or a fragment thereof) of an anti-NGAL antibody that can bind to the NGAL isoform can be used to detect any of the NGAL isoform that may be present in the test sample. Alternatively, a detectably labeled isoform of NGAL (or a fragment thereof, a variant thereof, or a fragment of a variant thereof), which is the same isoform as that which is being captured, can be used in a competitive assay format to compete with the NGAL isoform in the test sample in the determination of the presence, amount or concentration of NGAL isoform in a test sample.

Preferred antibodies for use in the context of the present disclosure include those described in U.S. patent application Ser. No. 12/104,413, which was filed Apr. 16, 2008.

Method for Determining the Presence, Amount or Concentration of at Least One Isoform of NGAL (or a fragment thereof) in a Test Sample The present disclosure provides a method for determining the presence, amount or concentration of at least one isoform of NGAL (or a fragment thereof) in a test sample. Any suitable assay as is known in the art can be used in the method. Examples include, but are not limited to, immunoassay, such as sandwich immunoassay (e.g., monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)), competitive inhibition immunoassay (e.g., forward and reverse), and fluorescence polarization immunoassay (FPIA). In a SELDI-based immunoassay, a capture reagent that specifically binds an NGAL isoform (or fragment thereof) of interest is attached to the surface of a mass spectrometry probe, such as a pre-activated protein chip array. The NGAL isoform is then specifically captured on the biochip, and the captured isoform is detected by mass spectrometry. Alternatively, the isoform can be eluted from the capture reagent and detected by traditional MALDI (matrix-assisted laser desorption/ionization) or by SELDI. A chemiluminescent microparticle immunoassay, in particular one employing the ARCHITECT® automated analyzer (Abbott Laboratories, Abbott Park, Ill.), is an example of a preferred immunoassay.

The method can be performed in a homogeneous or heterogeneous format. It will be recognized by those skilled in the art that an essential difference between the two formats exists. For example, homogeneous formats lack one or more steps to separate a complex between an analyte of interest in a test sample and a specific binding partner for the analyte of interest from uncomplexed binding partners and other components of a test sample. Further, homogeneous assays employ detectable labels. One or more characteristics of the signal generated from the detectable label is/are modulated by the formation of a complex between the analyte of interest in the test sample (i.e., an isoform of NGAL (or a fragment thereof)) and a specific binding partner for the analyte of interest (e.g., an antibody or fragment thereof that specifically binds to the particular isoform of NGAL (or a fragment thereof) of interest). Examples of such homogeneous assays that can be used include, but are not limited to, FPIA, enzyme multiplied immunoassay technique (EMIT), bioluminescence resonance energy transfer (BRET), homogeneous chemiluminescent assay, etc. In a homogeneous format, after the test sample is obtained from a subject, a first mixture is prepared. The mixture contains the test sample being assessed for one or more isoforms of NGAL (or fragments thereof) and a first specific binding partner that is labeled with a detectable label. The first specific binding partner can be an anti-NGAL antibody (or a fragment thereof).

Any suitable detectable label as is known in the art can be used. For example, a fluorescent label can be used in FPIA (see, e.g., U.S. Pat. Nos. 5,593,896, 5,573,904, 5,496,925, 5,359,093, and 5352803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)). Preferably, the acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In *Luminescence Biotechnology: Instruments and Applications*; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543,524 and 5,783,699 (each of which is incorporated herein by reference in its entirety for its teachings regarding same).

Alternatively, the acridinium compound preferably is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each incorporated herein by reference in their entireties for their teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, *High Throughput Bioanalytical Sample Preparation. Methods and Automation Strategies*, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007. Acridinium-9-carboxylate aryl esters can be dissolved in any suitable solvent, such as degassed anhydrous N,N-dimethylformamide (DMF) or aqueous sodium cholate.

Chemiluminescent assays can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and first specific binding partner labeled with the detectable label are added to form the mixture is not critical. After the first specific binding partner labeled with a detectable label and the test sample are added to form the first mixture, first specific binding partner-NGAL isoform complexes form.

Hydrogen peroxide can be generated in situ in the mixture or provided or supplied to the mixture before, simultaneously with, or after the addition of an above-described acridinium compound (specifically, the first specific binding partner labeled with the acridinium compound). Hydrogen peroxide can be generated in situ in a number of ways such as would be apparent to one skilled in the art.

Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the addition of the acridinium, e.g., acridinium-9-carboxamide or acridinium-9-carboxylate aryl ester, and the simultaneous or subsequent addition of at least one basic solution to the sample, a detectable signal, namely, a chemiluminescent signal, indicative of the presence of an isoform of NGAL is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of an isoform of NGAL in the sample can be quantified. Specifically, the amount of an isoform of NGAL in the sample is proportional to the intensity of the signal generated. The amount of an isoform of NGAL present can be quantified by comparing the amount of light generated to a standard curve for NGAL or by comparison to a reference standard. The standard curve can be generated using serial dilutions or solutions of known concentrations of NGAL by mass spectroscopy, gravimetric methods, and other techniques known in the art.

In a heterogeneous format, after the test sample is obtained from a subject, a first mixture is prepared. The mixture contains the test sample being assessed for one or more NGAL isoforms (or fragments thereof) and a first specific binding partner, wherein the first specific binding partner and any NGAL contained in the test sample form a first specific binding partner-NGAL complex. Preferably, the first specific binding partner is an anti-NGAL antibody or a fragment thereof. The order in which the test sample and the first specific binding partner are added to form the mixture is not critical. Preferably, the first specific binding partner is immobilized on a solid phase. The solid phase used in the immunoassay (for the first specific binding partner and, optionally, the second specific binding partner) can be any solid phase known in the art, such as, but not limited to, a magnetic particle, a bead, a test tube, a microtiter plate, a cuvette, a membrane, a scaffolding molecule, a film, a filter paper, a disc and a chip.

After the mixture containing the first specific binding partner-NGAL complex is formed, any unbound NGAL is removed from the complex using any technique known in the art. For example, the unbound NGAL can be removed by washing.

After any unbound NGAL is removed, a second specific binding partner is added to the mixture to form a first specific binding partner-NGAL-second specific binding partner complex. The second specific binding partner is preferably an anti-NGAL antibody. Moreover, also preferably, the second specific binding partner is labeled with or contains a detectable label. In terms of the detectable label, any detectable label known in the art can be used. For example, the detectable label can be a radioactive label (such as $^3$H, $^{125}$I, $^{35}$S, $^{14}$C, $^{32}$P, and $^{33}$P), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, 2$^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg. Preferably, however, the detectable label is an acridinium compound that can be used in a chemiluminescent assay.

After the formation of the first specific binding partner-NGAL-second specific binding complex, any unbound second specific binding partner (whether labeled or unlabeled) is removed from the complex using any technique known in the art. For example, the unbound second specific binding partner can be removed by washing.

Hydrogen peroxide can be generated in situ in the mixture or provided or supplied to the mixture before, simultaneously with, or after the addition of the above-described acridinium compound (specifically, the second specific binding partner labeled with the acridinium compound).

The timing and order in which the acridinium compound (specifically, the second specific binding partner labeled with the acridinium compound) and the hydrogen peroxide provided in or supplied to or generated in situ in the mixture is not critical. After the second specific binding partner labeled with a detectable label and the test sample are added to form the second mixture, first specific binding partner-autoantibody-second specific binding partner complexes form.

Upon the addition of the acridinium, e.g., acridinium-9-carboxamide or acridinium-9-carboxylate aryl ester, and the simultaneous or subsequent addition of at least one basic solution to the sample (as described above), a detectable signal, namely, a chemiluminescent signal, indicative of the presence of autoantibody is generated. Chemiluminescent signals generated can be detected using routine techniques known to those skilled in the art.

After any unbound second specific binding partner labeled with a detectable label is removed, a detectable signal from the detectable label is generated or emitted and then measured. Methods for generating signals from detectable labels and measuring the resulting signal generated are well-known to those skilled in the art. For example, a chemiluminescent signal can be generated after the addition of a basic solution. The amount of an isoform of NGAL in the test sample can be quantified based on the intensity of the signal generated. Specifically, the amount of an isoform of NGAL contained in a test sample is proportional to the intensity of the signal generated. Specifically, the amount of an isoform of NGAL present can be quantified based on comparing the amount of light generated to a standard curve for NGAL (or a fragment thereof) or by comparison to a reference standard. The standard curve can be generated using serial dilutions or solutions of NGAL (or a fragment thereof) of known concentration, by mass spectroscopy, gravimetrically and by other techniques known in the art.

Any suitable control composition can be used in the NGAL immunoassays. The control composition generally comprises the at least one NGAL isoform being assayed and any desirable additives. If more than one isoform of NGAL is being assayed, the NGAL isoforms can be combined in a single control composition or kept separate as appropriate. The mature, recombinantly produced, human NGAL (rhNGAL) is commercially available from Medical & Biological Laboratories Co., Ltd. (MBL; Japan). The hNGAL is recombinantly expressed in *E. coli*.

Accordingly, a method of determining the presence, amount or concentration of at least one NGAL isoform (or fragment thereof) that reacts with an anti-NGAL antibody (or a fragment thereof) in a test sample is provided. The method comprises assaying the test sample for at least one isoform of NGAL (or fragment thereof) that reacts with an anti-NGAL antibody (or a fragment thereof). The assay employs an anti-NGAL antibody (or a fragment thereof) and at least one detectable label. The assay comprises comparing a signal generated by the detectable label as a direct or indirect indication of the presence, amount or concentration of at least one isoform of NGAL that reacts with an anti-NGAL antibody (or a fragment thereof) in the test sample to a signal generated as a direct or indirect indication of the presence, amount or concentration of an isoform of NGAL (or a fragment thereof) in a control or calibrator. The calibrator is optionally part of a series of calibrators in which each of the calibrators differs from the other calibrators in the series by the concentration of the isoform of NGAL that reacts with an anti-NGAL antibody (or a fragment thereof). To the extent that each series of calibrating compositions contains only a single (or less than all) isoforms of NGAL, more than one series of calibrating compositions, such as one, two, three, four, five, six, or seven series, can be used.

The method can be adapted for use in an automated system or a semi-automated system.

The method can comprise (i) contacting the test sample with an anti-NGAL antibody (or a fragment thereof), which comprises a detectable label and binds to an isoform of NGAL (or fragment thereof) to form an anti-NGAL antibody (or a fragment thereof)/NGAL complex, and (ii) determining the presence, amount or concentration of at least one NGAL isoform, which reacts with an anti-NGAL antibody (or a fragment thereof), in the test sample by detecting or measuring the signal generated by the detectable label in the anti-NGAL antibody (or fragment thereof)/NGAL complex formed in (i). Preferably, the detectable label is an acridinium compound, such as an acridinium-9-carboxamide or an acridinium-9-carboxylate aryl ester.

The method can comprise (i) contacting the test sample with an anti-NGAL antibody (or a fragment thereof), which binds to at least one isoform of NGAL and which is optionally immobilized on a solid phase, so as to form an anti-NGAL antibody (or a fragment thereof)/NGAL complex, (ii) contacting the anti-NGAL antibody (or a fragment thereof)/NGAL complex with at least one detection antibody, which comprises a detectable label and binds to the NGAL to form an anti-NGAL antibody (or a fragment thereof)/NGAL/detection antibody complex, and (iii) determining the presence, amount or concentration of an isoform of NGAL in the test sample by detecting or measuring the signal generated by the detectable label in the anti-NGAL antibody (or a fragment thereof)/NGAL/detection antibody complex formed in (ii). Optionally, the method further comprises removing any unbound NGAL after step (i) and removing any unbound at least one detection antibody after step (ii).

Monoclonal and polyclonal antibodies (mAbs and pAbs, respectively) can be produced for use in immunoassays in accordance with methods known in the art. An isoform of NGAL (or fragment thereof), such as a recombinantly produced isoform of NGAL (or fragment thereof), in particular, a recombinantly produced isoform of human NGAL (or a fragment thereof), such as in a composition comprising an adjuvant, can be injected into a host animal, such as a rabbit, a goat, a mouse, a guinea pig, or a horse, at one or more sites. Further injections are made at the same or other sites at regular or irregular intervals thereafter with bleedings being taken to assess antibody titer until it is determined that optimal titer has been reached. The antibodies are obtained by either bleeding the host animal to yield a volume of antiserum, or by somatic cell hybridization techniques or other techniques known in the art. For example, the antibody-producing cells can be fused by standard somatic cell fusion procedures with immortalizing cells, such as myeloma cells, to yield hybridoma cells. Such techniques are well-known in the art, and include, for example, the hybridoma technique as originally developed by Kohler and Milstein, Nature 256: 495-497 (1975)), the human B cell hybridoma technique (Kozbar et al., Immunology Today 4: 72 (1983)), and the EBV-hybridoma technique to produce human mAbs (Cole et al., *Monoclonal Antibodies and Cancer Therapy*, Alan R. Liss, Inc. pp. 77-96 (1985)). The technology for producing monoclonal antibody hybridomas is well-known to those skilled in the art (see, e.g., Kenneth, in *Monoclonal Antibodies: A New Dimension in Biological Analyses*, Plenum Pub. Corp., New York (1980)). Alternatively, anti-NGAL antibodies can be commercially obtained from any one of a number of sources, such as R&D Systems (Minneapolis, Minn.) among others.

In a sandwich immunoassay format, typically at least two antibodies are used to separate and quantify an analyte of interest, in this case an isoform of NGAL (or a fragment thereof). More specifically, the two antibodies bind to different epitopes on the analyte of interest, thereby forming what is referred to as a "sandwich," i.e., antibody-analyte-antibody. One or more antibodies, which bind(s) to the analyte of interest and is/are typically bound to a substrate before or after contact with the analyte of interest, is/are referred to as the "capture antibody" or "capture antibodies," whereas one or more other antibodies, which is/are labeled and bind(s) to the analyte bound by the capture antibody, is/are referred to as the "detection antibody," "detection antibodies," "conjugate," or "conjugates." Preferably, the binding of one antibody to the analyte does not interfere with the binding of any other antibody to the analyte. Also, preferably, at least the capture antibody is present in a molar excess amount of the maximum amount of the analyte, i.e., an isoform of NGAL (or fragment thereof), expected to be present in a sample. While the detection antibody is typically labeled prior to contact with the analyte-capture antibody complex, the detection antibody can be labeled simultaneously with or subsequently to the formation of the analyte-capture antibody complex.

Generally speaking, a test sample being assayed for (for example, suspected of containing) isoforms of NGAL (or fragments thereof) can be contacted with at least one capture antibody (or antibodies) and at least one detection antibody (which is either a second detection antibody or a third detection antibody) either simultaneously or sequentially and in any order. For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

In the sandwich assay format, a test sample suspected of containing isoforms of NGAL (or fragments thereof) is first brought into contact with an at least one first capture antibody under conditions, which allow the formation of a first antibody/NGAL (or a fragment thereof) complex. If more than one capture antibody is used, a first multiple capture antibody/NGAL (or a fragment thereof) complex is formed. In a sandwich assay, the antibodies, preferably, the at least one capture antibody, are used in molar excess amounts of the maximum amount of NGAL (or a fragment thereof) expected in the test sample. For example, from about 5 µg/mL to about 1 mg/mL of antibody per mL of buffer (e.g., microparticle coating buffer) can be used.

Competitive inhibition immunoassays, which are often used to measure small analytes because binding by only one antibody is required, comprise sequential and classic formats. In a sequential competitive inhibition immunoassay a capture monoclonal antibody to an analyte of interest is coated onto a well of a microtiter plate. When the sample containing the analyte of interest is added to the well, the analyte of interest binds to the capture monoclonal antibody. After washing, a known amount of labeled (e.g., biotin or horseradish peroxidase (HRP)) analyte is added to the well. A substrate for an enzymatic label is necessary to generate a signal. An example of a suitable substrate for HRP is 3,3',5,5'-tetramethylbenzidine (TMB). After washing, the signal generated by the labeled analyte is measured and is inversely proportional to the amount of analyte in the sample. In a classic competitive inhibition immunoassay an monoclonal antibody to an analyte of interest is coated onto a well of a microtiter plate. However, unlike the sequential competitive inhibition immunoassay, the sample and the labeled analyte are added to the well at the same. Any analyte in the sample competes with labeled analyte for binding to the capture monoclonal antibody. After washing, the signal generated by the labeled analyte is measured and is inversely proportional to the amount of analyte in the sample.

Optionally, prior to contacting the test sample with the at least one capture antibody (for example, the first capture antibody), the at least one capture antibody can be bound to a solid support, which facilitates the separation of the first antibody/NGAL (or a fragment thereof) complex from the test sample. The substrate to which the capture antibody is bound can be any suitable solid support or solid phase that facilitates separation of the capture antibody-analyte complex from the sample. Examples include a well of a plate, such as a microtiter plate, a test tube, a porous gel (e.g., silica gel, agarose, dextran, or gelatin), a polymeric film (e.g., polyacrylamide), beads (e.g., polystyrene beads or magnetic beads), a strip of a filter/membrane (e.g., nitrocellulose or nylon), microparticles (e.g., latex particles, magnetizable microparticles (e.g., microparticles having ferric oxide or chromium oxide cores and homo- or hetero-polymeric coats and radii of about 1-10 microns). The substrate can comprise a suitable porous material with a suitable surface affinity to bind antigens and sufficient porosity to allow access by detection antibodies. A microporous material is generally preferred, although a gelatinous material in a hydrated state can be used. Such porous substrates are preferably in the form of sheets having a thickness of about 0.01 to about 0.5 mm, preferably about 0.1 mm. While the pore size may vary quite a bit, preferably the pore size is from about 0.025 to about 15 microns, more preferably from about 0.15 to about 15 microns. The surface of such substrates can be activated by chemical processes that cause covalent linkage of an antibody to the substrate. Irreversible binding, generally by adsorption through hydrophobic forces, of the antigen or the antibody to the substrate results; alternatively, a chemical coupling agent or other means can be used to bind covalently the antibody to the substrate, provided that such binding does not interfere with the ability of the antibody to bind an isoform of NGAL. Alternatively, the antibody can be bound with microparticles, which have been previously coated with streptavidin or biotin (e.g., using Power-Bind™-SA-MP streptavidin-coated microparticles (Seradyn, Indianapolis, Ind.)) or anti-species-specific mAbs. If necessary, the substrate can be derivatized to allow reactivity with various functional groups on the antibody. Such derivatization requires the use of certain coupling agents, examples of which include, but are not limited to, maleic anhydride, N-hydroxysuccinimide, and 1-ethyl-3-(3-dimethylaminopropyl)carbodiimide. If desired, one or more capture reagents, such as antibodies (or fragments thereof), each of which is specific for a particular isoform of NGAL can be attached to solid phases in different physical or addressable locations (e.g., such as in a biochip configuration (see, e.g., U.S. Pat. No. 6,225,047, Int'l Pat. App. Pub. No. WO 99/51773; U.S. Pat. No. 6,329,209; Int'l Pat. App. Pub. No. WO 00/56934, and U.S. Pat. No. 5,242,828). If the capture reagent is attached to a mass spectrometry probe as the solid support, the amount of NGAL isoform bound to the probe can be detected by laser desorption-ionization mass spectrometry. Alternatively, a single column can be packed with different beads, which are derivatized with the one or more capture reagents, thereby capturing the one or more isoforms of NGAL in a single place (see, antibody-derivatized, bead-based technologies, e.g., the xMAP technology of Luminex (Austin, Tex.)).

After the test sample being assayed for an isoform of NGAL (or a fragment thereof) is brought into contact with the at least one capture antibody (for example, the first capture antibody), the mixture is incubated in order to allow for the formation of a first antibody (or multiple antibody)-NGAL (or a fragment thereof) complex. The incubation can be carried out at a pH of from about 4.5 to about 10.0, at a temperature of from about 2° C. to about 45° C., and for a period from at least about one (1) minute to about eighteen (18) hours, preferably from about 1 to about 24 minutes, most preferably for about 4 to about 18 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After formation of the (first or multiple) capture antibody/NGAL (or a fragment thereof) complex, the complex is then contacted with at least one detection antibody (under conditions which allow for the formation of a (first or multiple) capture antibody/NGAL (or a fragment thereof)/second antibody detection complex). The at least one detection antibody can be the second, third, fourth, etc. antibodies used in the immunoassay. If the capture antibody/NGAL (or a fragment thereof) complex is contacted with more than one detection antibody, then a (first or multiple) capture antibody/NGAL (or a fragment thereof)/(multiple) detection antibody complex is formed. As with the capture antibody (e.g., the first capture antibody), when the at least second (and subsequent) detection antibody is brought into contact with the capture antibody/NGAL (or a fragment thereof) complex, a period of incubation under conditions similar to those described above is required for the formation of the (first or multiple) capture antibody/NGAL (or a fragment thereof)/(second or multiple) detection antibody complex. Preferably, at least one detection antibody contains a detectable label. The detectable label can be bound to the at least one detection antibody (e.g., the second detection antibody) prior to, simultaneously with, or after the formation of the (first or multiple) capture antibody/NGAL (or a fragment thereof)/(second or multiple) detection antibody complex. Any detectable label known in the art can be used (see discussion above, including Polak and Van Noorden (1997) and Haugland (1996)).

The detectable label can be bound to the antibodies either directly or through a coupling agent. An example of a coupling agent that can be used is EDAC (1-ethyl-3-(3-dimethylaminopropyl) carbodiimide, hydrochloride), which is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as CPSP-Acridinium Ester (i.e., 9-[N-tosyl-N-(3-carboxypropyl)]-10-(3-sulfopropyl)acridinium carboxamide) or SPSP-Acridinium Ester (i.e., N10-(3-sulfopropyl)-N-(3-sulfopropyl)-acridinium-9-carboxamide).

The (first or multiple) capture antibody/NGAL (or a fragment thereof)/(second or multiple) detection antibody complex can be, but does not have to be, separated from the remainder of the test sample prior to quantification of the label. For example, if the at least one capture antibody (e.g., the first capture antibody) is bound to a solid support, such as a well or a bead, separation can be accomplished by removing the fluid (of the test sample) from contact with the solid support. Alternatively, if the at least first capture antibody is bound to a solid support, it can be simultaneously contacted with the NGAL isoform (or a fragment thereof)-containing sample and the at least one second detection antibody to form a first (multiple) antibody/NGAL (or a fragment thereof)/second (multiple) antibody complex, followed by removal of the fluid (test sample) from contact with the solid support. If the at least one first capture antibody is not bound to a solid support, then the (first or multiple) capture antibody/NGAL (or a fragment thereof)/(second or multiple) detection antibody complex does not have to be removed from the test sample for quantification of the amount of the label.

After formation of the labeled capture antibody/NGAL (or a fragment thereof)/detection antibody complex (e.g., the first capture antibody/NGAL (or a fragment thereof)/second detection antibody complex), the amount of label in the complex is quantified using techniques known in the art. For example, if an enzymatic label is used, the labeled complex is reacted with a substrate for the label that gives a quantifiable reaction, such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high-speed photographic film, a CCD camera, etc. Once the amount of the label in the complex has been quantified, the concentration of NGAL isoform (or a fragment thereof) in the test sample is determined by use of a standard curve that has been generated using serial dilutions of NGAL (or a fragment thereof) of known concentration. Other than using serial dilutions of NGAL (or a fragment thereof), such as the isoform of NGAL (or fragment thereof) being assayed, the standard curve can be generated gravimetrically, by mass spectroscopy and by other techniques known in the art.

The NGAL assay can employ a monoclonal antibody sandwich that utilizes a capture antibody that preferentially binds to free NGAL isoform and excludes bound NGAL isoform, such as NGAL bound to metalloproteinase-9 (MMP-9) or gelatinase B. The amount of captured free NGAL can be detected with an acridinylated anti-NGAL monoclonal antibody.

FPIAs are based on competitive binding immunoassay principles. A fluorescently labeled compound, when excited by a linearly polarized light, will emit fluorescence having a degree of polarization inversely proportional to its rate of rotation. When a fluorescently labeled tracer-antibody complex is excited by a linearly polarized light, the emitted light remains highly polarized because the fluorophore is constrained from rotating between the time light is absorbed and the time light is emitted. When a "free" tracer compound (i.e., a compound that is not bound to an antibody) is excited by linearly polarized light, its rotation is much faster than the corresponding tracer-antibody conjugate produced in a competitive binding immunoassay. FPIAs are advantageous over RIAs inasmuch as there are no radioactive substances requiring special handling and disposal. In addition, FPIAs are homogeneous assays that can be easily and rapidly performed.

The method can further comprise diagnosing, prognosticating, or assessing the efficacy of a therapeutic/prophylactic treatment of a patient from whom the test sample was obtained. If the method further comprises assessing the efficacy of a therapeutic/prophylactic treatment of the patient from whom the test sample was obtained, the method optionally further comprises modifying the therapeutic/prophylactic treatment of the patient as needed to improve efficacy.

Generally, a predetermined level can be employed as a benchmark against which to assess results obtained upon assaying a test sample for at least one isoform of NGAL or a fragment thereof. Generally, in making such a comparison, the predetermined level is obtained by running a particular assay a sufficient number of times and under appropriate conditions such that a linkage or association of analyte (e.g., autoantibody) presence, amount or concentration with a particular stage or endpoint of a disease, disorder or condition (e.g., cardiovascular disease or renal disease) or with particular clinical indicia can be made. Typically, the predetermined level is obtained with assays of reference subjects (or populations of subjects).

In particular, with respect to a predetermined level as employed for monitoring disease progression and/or treatment, the concentration or amount of an isoform of NGAL or fragment thereof may be either "unchanged," "favorable" (or "favorably altered"), or "unfavorable" (or "unfavorably altered").

As used herein, the term "elevated" or "increased" refers to a concentration or amount in a test sample that is higher than a typical or normal level or range (e.g., predetermined level), or is higher that another reference level or range (e.g., earlier or baseline sample). The term "lowered" or "reduced" refers to a concentration or amount in a test sample that is higher than a typical or normal level or range (e.g., predetermined level), or is higher that another reference level or range (e.g., earlier or baseline sample). The term "altered" refers to a concentration or amount in a sample that is altered (increased or decreased) over a typical or normal level or range (e.g., predetermined level), or over another reference level or range (e.g., earlier or baseline sample).

The typical or normal level or range for isoforms of NGAL is defined in accordance with standard practice. Because the levels of NGAL isoforms in some instances will be very low, a so-called altered level or alteration can be considered to have occurred when there is any net change as compared to the typical or normal level or range, or reference level or range, that cannot be explained by experimental error or sample variation. Thus, the level measured in a particular sample will be compared with the level or range of levels determined in similar samples from a so-called normal subject. In this context, a "normal subject" is an individual with no detectable renal pathology, for example, and a "normal" (sometimes termed "control") patient or population is/are one(s) that exhibits no detectable renal pathology, for example. Furthermore, given that one or more isoforms of NGAL are not routinely found at high levels in the majority of the human population, a "normal subject" can be considered an individual with no substantial detectable increased or elevated concentration or amount of one or more isoforms of NGAL, and a "normal" (sometimes termed "control") patient or population is/are one(s) that exhibits no substantial detectable increased or elevated concentration or amount of one or more NGAL isoforms. An "apparently normal subject" is one in which NGAL isoforms have not been or are being assessed. The level of an analyte is said to be "elevated" when the analyte is normally undetectable (e.g., the normal level is zero, or within a range of from about 25 to about 75 percentiles of normal populations), but is detected in a test sample, as well as when the analyte is present in the test sample at a higher than normal level. Thus, inter alia, the disclosure provides a method of screening for a subject having, or at risk of having, renal disease, for example, as defined herein.

Any of the test methods as described herein can be performed in conjunction with one or more other tests including, but not limited to, physical examination, and/or the taking of a medical history to allow a differential diagnosis of renal disease. The various tests and parameters employed in diagnosing these disorders are well-known to those of skill in the art. Furthermore, any of the methods can be carried out on samples from asymptomatic subjects or subjects having one or more risk factors associated with, or symptoms of, renal disease.

In particular embodiments, when a subject is determined to have an unfavorable level of one or more NGAL isoforms, the subject optionally is assessed for one or more additional indicators of renal disease, such as proteinuria, heamaturia, serum creatine, cystatin C, S-adenosylhomocysteine, homocysteine, an abnormally high body mass index (BMI), obesity, and others as known in the art. However, such testing optionally can be carried out even when there has been no prior detection of an unfavorable level of one or more isoforms of NGAL (or a fragment thereof).

Accordingly, the methods described herein also can be used to determine whether or not a subject has or is at risk of developing a renal disease. Specifically, such a method can comprise the steps of:

(a) determining the concentration or amount in a test sample from a subject of at least one isoform of NGAL (or a fragment thereof) (e.g., using the methods described herein, or methods known in the art); and (b) comparing the concentration or amount of at least one isoform of NGAL (or fragment thereof) determined in step (a) with a predetermined level, wherein, if the concentration or amount of the one or more isoforms of NGAL determined in step (a) is favorable with respect to a predetermined level, then the subject is determined not to have or be at risk for a renal disease. However, if the concentration or amount of the one or more isoforms of NGAL determined in step (a) is unfavorable with respect to the predetermined level, then the subject is determined to have or be at risk for a renal disease.

Additionally, provided herein is method of monitoring the progression of disease in a subject. Optimally the method comprising the steps of:

(a) determining the concentration or amount in a test sample from a subject of at least one isoform of NGAL;

(b) determining the concentration or amount in a later test sample from the subject of at least one isoform of NGAL; and (c) comparing the concentration or amount of at least one isoform of NGAL as determined in step (b) with the concentration or amount of at least one isoform of NGAL determined in step (a), wherein if the concentration or amount determined in step (b) is unchanged or is unfavorable when compared to the concentration or amount of at least one isoform of NGAL determined in step (a), then the disease in the subject is determined to have continued, progressed or worsened. By comparison, if the concentration or amount of at least one isoform of NGAL as determined in step (b) is favorable when compared to the concentration or amount of at least one isoform of NGAL as determined in step (a), then the disease in the subject is determined to have discontinued, regressed or improved.

Optionally, the method further comprises comparing the concentration or amount of at least one isoform of NGAL as determined in step (b), for example, with a predetermined level. Further, optionally the method comprises treating the subject with one or more pharmaceutical compositions for a period of time if the comparison shows that the concentration or amount of at least one isoform of NGAL as determined in step (b), for example, is unfavorably altered with respect to the predetermined level.

Still further, the methods can be used to monitor treatment in a subject receiving treatment with one or more pharmaceutical compositions. Specifically, such methods involve providing a first test sample from a subject before the subject has been administered one or more pharmaceutical compositions. Next, the concentration or amount in a first test sample from a subject of at least one isoform of NGAL is determined (e.g., using the methods described herein or as known in the art). After the concentration or amount of at least one isoform of NGAL is determined, optionally the concentration or amount of at least one isoform of NGAL is then compared with a predetermined level. If the concentration or amount of the at least one isoform of NGAL as determined in the first test sample is lower than the predetermined level, then the subject is not treated with one or more pharmaceutical compositions. However, if the concentration or amount of the at least one isoform of NGAL as determined in the first test sample is higher than the predetermined level, then the subject is treated with one or more pharmaceutical compositions for a period of time. The period of time that the subject is treated with the one or more pharmaceutical compositions can be determined by one skilled in the art (for example, the period of time can be from about seven (7) days to about two years, preferably from about fourteen (14) days to about one (1) year).

During the course of treatment with the one or more pharmaceutical compositions, second and subsequent test samples are then obtained from the subject. The number of test samples and the time in which said test samples are obtained from the subject are not critical. For example, a second test sample could be obtained seven (7) days after the subject is first administered the one or more pharmaceutical compositions, a third test sample could be obtained two (2) weeks after the subject is first administered the one or more pharmaceutical compositions, a fourth test sample could be obtained three (3) weeks after the subject is first administered the one or more pharmaceutical compositions, a fifth test sample could be obtained four (4) weeks after the subject is first administered the one or more pharmaceutical compositions, etc.

After each second or subsequent test sample is obtained from the subject, the concentration or amount of at least one isoform of NGAL is determined in the second or subsequent test sample is determined (e.g., using the methods described herein or as known in the art). The concentration or amount of at least one isoform of NGAL as determined in each of the second and subsequent test samples is then compared with the concentration or amount of at least one isoform of NGAL as determined in the first test sample (e.g., the test sample that was originally optionally compared to the predetermined level). If the concentration or amount of at least one isoform of NGAL as determined in step (c) is favorable when compared to the concentration or amount of at least one isoform of NGAL as determined in step (a), then the disease in the subject is determined to have discontinued, regressed or improved, and the subject should continue to be administered the one or pharmaceutical compositions of step (b). However, if the concentration or amount determined in step (c) is unchanged or is unfavorable when compared to the concentration or amount of at least one isoform of NGAL as determined in step (a), then the disease in the subject is determined to have continued, progressed or worsened, and the subject should be treated with a higher concentration of the one or more pharmaceutical compositions administered to the subject in step (b) or the subject should be treated with one or more pharmaceutical compositions that are different from the one or more pharmaceutical compositions administered to the subject in step (b). Specifically, the subject can be treated with one or more pharmaceutical compositions that are different from the one or more pharmaceutical compositions that the subject had previously received to decrease or lower said subject's NGAL isoform levels.

Generally, for assays in which repeat testing may be done (e.g., monitoring disease progression and/or response to treatment), a second or subsequent test sample is obtained at a period in time after the first test sample has been obtained from the subject. Specifically, a second test sample from the subject can be obtained minutes, hours, days, weeks or years after the first test sample has been obtained from the subject. For example, the second test sample can be obtained from the subject at a time period of about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5 years, about 6.0 years, about 6.5 years, about 7.0 years, about 7.5 years, about 8.0 years, about 8.5 years, about 9.0 years, about 9.5 years or about 10.0 years after the first test sample from the subject is obtained. When used to monitor disease progression, the above assay can be used to monitor the progression of disease in subjects suffering from acute conditions. Acute conditions, also known as critical care conditions, refer to acute, life-threatening diseases or other critical medical conditions involving, for example, the cardiovascular system or excretory system. Typically, critical care conditions refer to those conditions requiring acute medical intervention in a hospital-based setting (including, but not limited to, the emergency room, intensive care unit, trauma center, or other emergent care setting) or administration by a paramedic or other field-based medical personnel. For critical care conditions, repeat monitoring is generally done within a shorter time frame, namely, minutes, hours or days (e.g., about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days or about 7 days), and the initial assay likewise is generally done within a shorter timeframe, e.g., about minutes, hours or days of the onset of the disease or condition.

The assays also can be used to monitor the progression of disease in subjects suffering from chronic or non-acute conditions. Non-critical care or, non-acute conditions, refers to conditions other than acute, life-threatening disease or other critical medical conditions involving, for example, the cardiovascular system and/or excretory system. Typically, non-acute conditions include those of longer-term or chronic duration. For non-acute conditions, repeat monitoring generally is done with a longer timeframe, e.g., hours, days, weeks, months or years (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years), and the initial assay likewise generally is done within a longer time frame, e.g., about hours, days, months or years of the onset of the disease or condition.

Furthermore, the above assays can be performed using a first test sample obtained from a subject where the first test sample is urine. Optionally the above assays can then be repeated using a second test sample obtained from the subject where the second test sample is something other than urine, such as serum or plasma. The results obtained from the assays using the first test sample and the second test sample can be compared. The comparison can be used to assess the status of a disease or condition in the subject.

Moreover, the present disclosure also relates to methods of determining whether a subject predisposed to or suffering from a disease (e.g., renal disease) will benefit from treatment. In particular, the disclosure relates to NGAL companion diagnostic methods and products. Thus, the method of "monitoring the treatment of disease in a subject" as described herein further optimally also can encompass selecting or identifying candidates for therapy.

Thus, in particular embodiments, the disclosure also provides a method of determining whether a subject having, or at risk for, renal disease is a candidate for therapy. Generally, the subject is one who has experienced some symptom of renal disease or who has actually been diagnosed as having, or being at risk for, renal disease, and/or who demonstrates an unfavorable concentration or amount of at least one isoform of NGAL or a fragment thereof, as described herein.

The method optionally comprises an assay as described herein, where analyte is assessed before and following treatment of a subject with one or more pharmaceutical compositions (e.g., particularly with a pharmaceutical related to a mechanism of action involving NGAL), with immunosuppressive therapy, or by immunoabsorption therapy, or where analyte is assessed following such treatment and the concentration or the amount of analyte is compared against a predetermined level. An unfavorable concentration of amount of analyte observed following treatment confirms that the subject will not benefit from receiving further or continued treatment, whereas a favorable concentration or amount of analyte observed following treatment confirms that the subject will benefit from receiving further or continued treatment. This confirmation assists with management of clinical studies, and provision of improved patient care.

It goes without saying that while certain embodiments herein are advantageous when employed to assess renal disease, the assays and kits also optionally can be employed to assess NGAL isoforms in other diseases, disorders and conditions, e.g., cancer, sepsis, and any disease, disorder or condition that might involve an assessment of NGAL.

More specifically, in addition to assessment of renal disorders, diseases and injuries (see, e.g., U.S. Pat. App. Pub. Nos. 2008/0090304, 2008/0014644, 2008/0014604, 2007/0254370, and 2007/0037232), the assay and assay components as described herein optionally also can be employed in any other NGAL assay or in any other circumstance in which an assessment of the presence, amount or concentration of one or more NGAL isoforms might prove helpful: e.g., cancer-related assays (e.g., generally, or more specifically including but not limited to pancreatic cancer, breast cancer, ovarian/uterine cancer, leukemia, colon cancer, and brain cancer; see, e.g., U.S. Pat. App. Pub. No. 2007/0196876; see, also, U.S. Pat. Nos. 5,627,034 and 5,846,739); diagnosis of systemic inflammatory response syndrome (SIRS), sepsis, severe sepsis, septic shock and multiple organ dysfunction syndrome (MODS) (see, e.g., U.S. Pat. App. Pub. Nos. 2008/0050832 and 2007/0092911; see, also, U.S. Pat. No. 6,136,526); hematology applications (e.g., estimation of cell type); assessment of preeclampsia, obesity (metabolic syndrome), insulin resistance, hyperglycemia, tissue remodeling (when complexed with MMP-9; see, e.g., U.S. Pat. App. Pub. No. 2007/0105166 and U.S. Pat. No. 7,153,660), autoimmune diseases (e.g., rheumatoid arthritis, inflammatory bowel disease, multiple sclerosis), irritable bowel syndrome (see, e.g., U.S. Pat. App. Pub. Nos. 2008/0166719 and 2008/0085524), neurodegenerative disease, respiratory tract disease, inflammation, infection, periodontal disease (see, e.g., U.S. Pat. No. 5,866,432), and cardiovascular disease including venous thromboembolic disease (see, e.g., U.S. Pat. App. Pub. Nos. 2007/0269836), among others. Moreover, any of the teachings of U.S. Provisional App. Nos. 60/981,470, 60/981,471 and 60/981,473, all filed on Oct. 19, 2007, and U.S. patent application Ser. Nos. 12/104,408, 12/104,410, and 12/104,413, all filed on Apr. 16, 2008, with respect to assay rare reagents NGAL antigen, anti-NGAL antibody, and an NGAL assay can be applied in the methods and kits as described herein and are each incorporated by reference in their entireties for their teachings regarding same.

Kits

A kit for assaying a patient urine sample for one or more isoforms of NGAL (or fragments thereof) is also provided. The kit comprises one or more components for assaying the patient urine sample for NGAL isoforms (or fragments thereof) and instructions for assaying the patient urine sample for NGAL isoforms (or fragments thereof). The kit can comprise one or more components for assaying the patient urine sample for NGAL isoforms by immunoassay, e.g., chemiluminescent microparticle immunoassay, and instructions for assaying the patient urine sample for NGAL isoforms by immunoassay, e.g., chemiluminescent microparticle immunoassay. For example, the kit can comprise at least one capture antibody and/or at least one detection antibody. Alternatively or additionally, the kit can comprise a calibrator or control, e.g., purified, and optionally lyophilized, NGAL isoform(s), and/or at least one container (e.g., tube, microtiter plates or strips, which can be already coated with an anti-NGAL monoclonal antibody) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions can also contain instructions for generating a standard curve or a reference standard for purposes of quantifying one or more NGAL isoforms. Such instructions optionally can be in printed form or on CD, DVD, or other format of recorded media.

Any antibodies, which are provided in the kit, such as antibodies specific for NGAL, can incorporate a detectable label, such as a fluorophore, radioactive moiety, enzyme, biotin/avidin label, chromophore, chemiluminescent label, or the like, or the kit may include reagents for labeling the antibodies or reagents for detecting the antibodies (e.g., detection antibodies) and/or for labeling the analytes or reagents for detecting the analyte. The antibodies, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine sample). Where appropriate, the kit optionally also can contain reaction vessels, mixing vessels, and other components that facilitate the preparation of reagents or the test sample. The kit can also include one or more instrument for assisting with obtaining a test sample, such as a cup.

Preferably, the detectable label is at least one acridinium compound as described herein. The kit can comprise at least one acridinium-9-carboxamide, at least one acridinium-9-carboxylate aryl ester, or any combinations thereof. If the detectable label is at least one acridinium compound, the kit also can comprise a source of hydrogen peroxide, such as a buffer, solution, and/or at least one basic solution. If desired, the kit can contain a solid phase, such as a magnetic particle, bead, test tube, microtiter plate, cuvette, membrane, scaffolding molecule, film, filter paper, disc or chip.

Adaptation of Method and Assay Kit

The kit (or components thereof), as well as the method of determining the presence, amount or concentration of one or more isoforms of NGAL (or fragments thereof) in a test sample by an assay as described above, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., an anti-NGAL antibody or fragment thereof) is attached (which can impact sandwich formation and analyte reactivity), and the length and timing of the capture, detection and/or any optional wash steps. Whereas a non-automated format, such as an ELISA, may require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format such as an ELISA may incubate a detection antibody, such as the conjugate reagent, for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an NGAL isoform assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising the second detection antibody labeled with alkaline phosphatase (or other label). Within the fluid pouch of the cartridge is an aqueous reagent that includes p-aminophenol phosphate.

In operation, a sample suspected of containing NGAL isoforms is added to the holding chamber of the test cartridge and the cartridge is inserted into the I-STAT® reader. After the second antibody (detection antibody) has dissolved into the sample, a pump element within the cartridge forces the sample into a conduit containing the chip. Here it is oscillated to promote formation of the sandwich between the capture antibody, NGAL isoform(s), and the labeled detection antibody. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount or concentration of at least one isoform of NGAL in the sample by means of an embedded algorithm and factory-determined calibration curve.

It further goes without saying that the methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent.

Anti-NGAL Antibody Pharmaceutical Composition

A pharmaceutical composition comprising an isolated antibody or fragment thereof that specifically binds to a particular isoform of NGAL (or a fragment thereof) is also provided. The composition can comprise more than one antibody (or fragment thereof), wherein each antibody binds the same or different isoforms of NGAL. The composition also comprises a pharmaceutically acceptable carrier, diluent, and/or excipient. Suitable carriers, diluents, and/or excipients are well-known in the art (see, e.g., Remington's Pharmaceutical Sciences, $20^{th}$ edition, Gennaro, editor, Lippincott, Williams & Wilkins, Philadelphia, Pa., 2000). Optionally, the composition further comprises another active agent and/or an adjuvant. The pharmaceutical composition is optionally part of a kit comprising one or more containers in which the antibody, another active agent and/or the adjuvant can be present in the same or different containers.

Recombinant forms of antibodies, such as chimeric and humanized antibodies, can be used in pharmaceutical compositions to minimize the response by a human patient to the antibody. When antibodies produced in non-human subjects or derived from expression of non-human antibody genes are used therapeutically in humans, they are recognized to varying degrees as foreign, and an immune response may be generated in the patient. One approach to minimize or eliminate this immune reaction is to produce chimeric antibody derivatives, namely, antibody molecules that combine a non-human animal variable region and a human constant region. Such antibodies retain the epitope binding specificity of the original monoclonal antibody but may be less immunogenic when administered to humans and, therefore, more likely to be tolerated by the patient.

Chimeric monoclonal antibodies can be produced by recombinant DNA techniques known in the art. For example, a gene encoding the constant region of a non-human antibody molecule is substituted with a gene encoding a human constant region (see, for example, Int'l Pat. App. Pub. No. PCT/US86/02269, European Pat. App. 184,187, or European Pat. App. 171,496).

A chimeric antibody can be further "humanized" by replacing portions of the variable region not involved in antigen binding with equivalent portions from human variable regions. General reviews of "humanized" chimeric antibodies can be found in Morrison, Science 229: 1202-1207 (1985), and Oi et al., BioTechniques 4: 214 (1986). Such methods include isolating, manipulating, and expressing the nucleic acid sequences that encode all or part of an immunoglobulin variable region from at least one of a heavy or light chain. The cDNA encoding the humanized chimeric antibody, or fragment thereof, can then be cloned into an appropriate expression vector. Suitable "humanized" antibodies can be alternatively produced by complementarity determining region (CDR) substitution (see, for example, U.S. Pat. No. 5,225,539; Jones et al., Nature 321: 552-525 (1986); Verhoeyen et al., Science 239 (4847): 1534-1536 (1988); and Beidler et al., J. Immunol. 141: 4053-4060 (1988)).

Epitope imprinting also can be used to produce a "human" antibody polypeptide dimer that retains the binding specificity of the antibodies (e.g., hamster antibodies) specific for the human NGAL or antigenically reactive fragment thereof. Briefly, a gene encoding a non-human variable region (VH) with specific binding to an antigen and a human constant region (CH1), is expressed in E. coli and infected with a phage library of human Vλ, genes. Phage displaying antibody fragments are then screened for binding to the human NGAL protein. Selected human Vλ genes are recloned for expression of Vλ.Cλ. chains and E. coli harboring these chains are infected with a phage library of human VHCH1 genes and the library is subject to rounds of screening with antigen-coated tubes (see, e.g., Int'l Pat. App. Pub. No. WO 93/06213).

For administration to an animal, the pharmaceutical composition can be formulated for administration by a variety of routes. For example, the composition can be formulated for oral, topical, rectal or parenteral administration or for administration by inhalation or spray. The term "parenteral" as used herein includes subcutaneous, intravenous, intramuscular, intrathecal, and intrasternal injection and infusion techniques. Various diagnostic compositions and pharmaceutical compositions suitable for different routes of administration and methods of preparing pharmaceutical compositions are known in the art and are described, for example, in "Remington: The Science and Practice of Pharmacy" (formerly "Remington's Pharmaceutical Sciences"); Gennaro, A., Lippincott, Williams & Wilkins, Philadelphia, Pa. (2000). The pharmaceutical composition can be used in the treatment of various conditions in animals, including humans.

The pharmaceutical composition preferably comprises a therapeutically or prophylactically effective amount of one or more anti-NGAL antibodies (or fragments thereof). The term "therapeutically or prophylactically effective amount" as used herein refers to an amount of an anti-NGAL antibody needed to treat, ameliorate, inhibit the onset, delay or slow the progression, or prevent a targeted disease or condition, or to exhibit a detectable therapeutic or preventative effect. For anti-NGAL antibody, the therapeutically or prophylactically effective amount can be estimated initially, for example, either in cell culture assays or in animal models, usually in rodents, rabbits, dogs, pigs or primates. The animal model also can be used to determine the appropriate concentration range and route of administration. Such information then can be used to determine useful doses and routes for administration in the animal to be treated, including humans.

Examples of other active agents, which can be included in the pharmaceutical composition, include, but are not limited to, interleukin-18 (IL-18), kidney injury molecule-1 (KIM-1), cystatin C, and liver type fatty acid binding protein 1 (L-FABP 1) for the treatment of acute kidney injury, and procalcitonin for the treatment of sepsis.

The pharmaceutical composition comprising at least one antibody (or fragment thereof) that specifically binds to a particular isoform of NGAL (or a fragment thereof) can be provided as a therapeutic kit or pack. Individual components of the kit can be packaged in separate containers, associated with which, when applicable, can be a notice in the form prescribed by a governmental agency regulating the manufacture, use or sale of pharmaceuticals or biological products, which notice reflects approval by the agency of manufacture, use or sale for human or animal administration. The kit can optionally further contain one or more other active agents for use in combination with the pharmaceutical composition comprising the at least one antibody (or fragment thereof). The kit can optionally contain instructions or directions outlining the method of use or dosing regimen for the pharmaceutical composition comprising the at least one antibody (or fragment thereof) and/or additional active agents or adjuvants.

When one or more components of the kit are provided as solutions, for example an aqueous solution, or a sterile aqueous solution, the container means can itself be an inhalant, syringe, pipette, eye dropper, or other such like apparatus, from which the solution can be administered to a subject or applied to and mixed with the other components of the kit.

The components of the kit also can be provided in dried or lyophilized form, and the kit can additionally contain a suitable solvent for reconstitution of the lyophilized components. Irrespective of the number or types of containers, the kit also can comprise an instrument for assisting with the administration of the composition to a patient. Such an instrument can be an inhalant, a syringe, a pipette, a forceps, a measuring spoon, an eye dropper, or a similar, medically approved, delivery vehicle. Accordingly, the pharmaceutical composition optionally can be part of a kit comprising one or more containers in which the antibody (or fragment thereof), another active agent and/or the adjuvant can be present in the same or different containers.

Method of Prophylactic or Therapeutic Treatment

A method of treating a patient in therapeutic or prophylactic need of an antagonist of one or more isoforms of NGAL is also provided. The method comprises administering to the patient a pharmaceutical composition comprising a therapeutically or prophylactically effective amount of an antagonist of one or more isoforms of NGAL, such as an antibody (or fragment thereof), which specifically binds to a particular isoform of NGAL (or a fragment thereof). The composition further comprises a pharmaceutically acceptable carrier, diluent, and/or excipient. Optionally, the composition further comprises another active agent and/or an adjuvant. The method can prove useful in the treatment of renal injury or disease, such as acute (e.g., in combination with IL-18, KIM-1, cystatin C, or L-FABP 1) or chronic renal injury or disease, progressive kidney failure, irritable bowel syndrome, inflammation, sepsis (e.g., in combination with procalcitonin), and cancer, among others as discussed in the "BACKGROUND" herein. The appropriate dosage, route of administration, and frequency of administration can be determined in accordance with routine methods of dosage-range finding and the like as known in the art and as discussed above.

EXAMPLES

The following examples serve to illustrate the present disclosure. The examples are not intended to limit the scope of the claimed invention in any way.

Example 1

This example describes the enrichment of NGAL in a pool of urine samples, which were obtained from human patients in intensive care and which contained high levels of NGAL. The samples from one or more Intensive Care Units were collected by and obtained from Bioreclamation, Inc., 290 Duffy Ave, Hicksville, N.Y. 11801 (Catalog Number HMU-RINE-ICU).

Seven of the urine samples were pooled (~30 mL) and mixed by rotating for 10 minutes. The mixture was centrifuged at 2,400 rpm for 15 minutes. The supernatant was decanted, and an 800 µL sample was removed and stored overnight at 2-8° C.

The sample was brought to room temperature, and the pH was adjusted to 3.0. Since the initial pH of the sample was 7.66, 335 µL of 6 N HCl were added to the sample drop-wise with mixing until a final pH of 2.92 was obtained.

The sample was then placed on ice and kept on ice until the temperature of the sample was below 5° C. Then 43.36 mL of ethanol (EtOH; 60%) were added to the sample drop-wise over 15 minutes. The sample was swirled and placed back on ice for 30 minutes. After being removed from ice, the sample was swirled to mix and poured into two 50 mL polypropylene centrifuge tubes. The tubes were centrifuged at 3,500 rpm for 30 minutes.

The supernatant (urine/EtOH) from both tubes was decanted into a polypropylene bottle. Zinc acetate solution (ZnOAc; 1 M) was added to the acidified urine/EtOH supernatant to a final concentration of 20 mM, and the sample was rotated to mix for 30 minutes. Afterwards, the sample was centrifuged at 3,500 rpm for 30 minutes. The supernatant was decanted. Regeneration buffer (50 mM EDTA, pH 5.0; 2 mL) was added to the pellet, and the tube was rotated to dissolve the pellet.

Example 2

This example describes further enrichment of the "enriched sample" of Example 1.

The enriched sample from Example 1 was subjected to a variety of further enrichment strategies employing ultra-filtration buffer exchange, size-exclusion chromatography, and ammonium sulfate precipitation. A portion of the enriched sample was subjected to size-exclusion chromatography to confirm by ARCHITECT® (Abbott Laboratories, Abbott Park, Ill.) assay that the NGAL activity in this extract existed as a single-size population with elution properties correlating to the size of the monomeric NGAL protein.

A portion of the enriched sample was processed with ultrafiltration buffer exchange followed by size-exclusion chromatography to obtain further enriched samples for analysis by 2DE. Specifically, these processes included an exchange to phosphate-buffered saline (PBS) buffer matrix with a Millipore Ultra-4 10 kDa ultrafiltration centrifugal device (Millipore Biosciences, Temecula, Calif.) and sizing chromatography through a GE Healthcare Superdex 75 column on a GE Healthcare Akta Purifier system (GE Healthcare, Piscataway, N.J.).

Another portion of the enriched sample was processed with ammonium sulfate precipitation followed by ultra-filtration buffer exchange. The NGAL protein was precipitated with the addition of ammonium sulfate at a concentration of 60% wt./vol. and incubated at 2-8° C. for 16 hours. The NGAL-containing precipitate was centrifuged, and the resulting pellet was dissolved with a minimal volume of PBS. The PBS-reconstituted ammonium sulfate precipitate containing NGAL protein was then treated with multiple exchanges of PBS using a Millipore Ultra-4 10 kDa ultrafiltration centrifugal device to obtain a sample for analysis by 2DE. A portion of the enriched sample was analyzed by 2DE following buffer exchange with the Millipore Ultra-4 10 kDa ultrafiltration centrifugal device alone.

Example 3

This example describes the 2DE of samples of NGAL further enriched in accordance with the methods of Example 2.

Two-dimensional electrophoresis was used to determine the charge and size properties of the NGAL in the samples of Example 2. Charge (pI) and size (MW) properties of NGAL-active protein isoforms were determined by correlation of migration in both dimensions to internal calibration standards added to each sample. NGAL-active protein amongst all spots in 2DE was identified by Western blot using both monoclonal and polyclonal antibodies raised against purified recombinant human NGAL protein. Regardless of the enrichment process applied to the enriched sample, the resulting charge and size distributions of NGAL-active protein isoforms were equivalent. Quantities and type of non-NGAL-active proteins varied in samples from different enrichment processes, but the NGAL-active isoform distribution remained constant across all described enrichment methods. Application of a sequential dual blot detection method to analysis of the 2DE gels confirmed the identity of NGAL in the enriched protein mixture.

The resulting pI values determined for five isoforms of NGAL were 5.9, 6.9, 8.3, 8.8 and 9.1, all at a MW range of 25-26 kDa. Molecular weight values determined for the NGAL-active isoforms correlated well with the predicted molecular weight of the monomeric polypeptide translated by the human NGAL gene. However, the charge distribution of the NGAL-active isoforms enriched from human urine reached far more into the acidic range than predicted for the polypeptide sequence or simple post-translationally modified forms of the translated human NGAL polypeptide.

Purified samples of human NGAL from non-urine sources, such as recombinant protein produced in *E. coli* and mouse myeloma cell culture, as well as native NGAL isolated from human neutrophils, were also analyzed with the same 2DE methods. The NGAL protein from all of these sources did not yield an equivalent charge distribution of NGAL isoforms as seen for NGAL enriched from human urine. The charge determinations for NGAL isoforms from these alternate sources were all above pI=8.0.

A purified sample of recombinant human NGAL produced in CHO cells (i.e., CHO cell line that has been deposited with the American Type Culture Collection (ATCC) at 10801 University Boulevard, Manassas, Va. 20110-2209 on Jan. 23, 2007 and received ATCC Accession No. PTA-8168) and purified using metal-ion affinity to an appended His-tag sequence was also analyzed with the same 2DE methods. The NGAL isoform distribution of this recombinant sample displayed seven detected species with a MW range of 25.9-27.4 kDa and a pI range of 5.6 to 9.1. Other preparations of NGAL from this CHO-recombinant source displayed similar MW ranges, although the span and distribution of pI values for the detected isoforms varied significantly between preparations.

Example 4

This example describes pre-treatment of a pool of urine samples, which are obtained from presumed healthy human patients.

Similar processes for extraction, enrichment, and 2DE analysis are used to elucidate charge and size properties of NGAL isoforms from a pool of urine samples obtained from presumed healthy human subjects. In this case, since the total NGAL concentration is expected to be significantly lower than what was found in the pool of urine samples of Example 1, a pre-processing step involving large-scale buffer exchange and protein concentration with a cross-flow diafiltration system fit with a 5 kDa, 0.6 m$^2$ Sartorius membrane cassette (Sartorius AG, Goettingen, Germany) is applied prior to the extraction and enrichment processes.

Example 5

This example describes the isolation, amino acid sequencing, and glycan content of NGAL isoforms.

A larger-scale extraction, enrichment, and 2DE separation is used to obtain sufficient quantities of individual NGAL isoforms for determination of amino acid sequence and glycan content. Amino acid sequence information is obtained directly from 2DE spots representing an individual NGAL isoform using well-established in-gel proteolysis and extraction methods followed by LC/MS/MS or automated N-terminal sequencing (Edman degradation) analyses. Glycan structural information is also obtained from individual NGAL isoforms using in-gel glycosidase digestion and extraction methods followed by LC/MS/MS or glycan profiling and total monosaccharide LC analyses. Where quantities of resolved individual NGAL isoforms from 2DE are insufficient for amino acid or glycan compositional analyses, a preparative chromatographic method employing charge-based separation, such as ion-exchange or chromatofocusing, is applied to resolve larger quantities of NGAL isoforms.

Example 6

This example describes the production of and sequencing of a monoclonal antibody that specifically binds to an NGAL isoform.

NGAL isoforms are isolated from urine. These isoforms are separated from one another by SDS-PAGE, IEF, 2DE, Column Isoelectric Focusing, or a combination of these and other methods. Isolation of each isoform need not be complete to ensure production of a monoclonal antibody.

Once isolated, the separated isoforms are injected intramuscularly or intraperitoneally into BALB/c mice. The injected material may be a solution of an isolated NGAL isoform or a minced, pulverized gel slice. Mice responding to the immunization are tested for reactivity by any of a number of possible tests, including, but not limited to ELISA, microtiter, Western blot, 2-dimensional Western blot, or dot blot. Spleens from these mice are isolated, and the B cells are fused with Sp2/0 Ag14 mouse myeloma cells using various modifications of the method of Kohler and Milstein. Fusions producing an appropriate antibody are screened using 2-dimensional Western blot to identify antibodies that specifically bind to one or a subset of isoforms.

Once fusions secreting appropriate antibodies are identified these are subcloned by limiting dilution to produce clones secreting a single monoclonal antibody. These clones are screened once again using the 2-dDimensional Western blot to assure selection of clones secreting antibody to a single or limited subset of isoforms.

Final selected clones can be further screened for isotype using any of several commercially available isotype-identifying assays. Monoclonal antibodies with specific subtypes, for example IgG1s, can be further specifically selected as better suited for particular purposes, such as for use as F(ab')2 conjugates.

Once the isotype of any particular monoclonal antibody is know, sequencing of that monoclonal is accomplished via RT-PCR sequencing. Since antibodies have common, constant sequences, common DNA sequences within the antibodies and upstream and downstream of the coding sequences are known. These sequences can serve as the source of PCR amplification and DNA sequencing primers. The first step to determining the sequence of any monoclonal antibody is isolation of messenger RNA from the clone cells secreting the monoclonal antibody. Once RNA has been isolated, a short DNA or RNA primer homologus to the appropriate downstream constant region can be used with reverse transcriptase to generate a specific single-stranded DNA copy of the RNA. DNA polymerase is then used with a common upstream primer to produce a specific double-stranded cDNA (copy DNA) specific for the monoclonal antibody. The original downstream and upstream primers, or other interior constant region primers, then can be used with the cDNA and a thermostable DNA polymerase, such as Taq DNA Polymerase, recombinant variants of Taq DNA Polymerase, *Pyrococcus* DNA Polymerase or recombinant variants of *Pyrococcus* DNA Polymerase to produce a large amount of cDNA specific for the monoclonal antibody. This cDNA then can be used as template with any of a number of commercially available DNA sequencing kits and appropriate sequencing equipment to determine the DNA sequence of the monoclonal antibody. The amino acid sequence of the monoclonal antibody and, specifically, the variable regions of the monoclonal antibody can be deduced from the DNA sequence using the universal code.

Alternatively, the amino acid sequence of the monoclonal antibody can be determined using LC/MS/MS and collisional degradation of the protein molecules. In this method purified monoclonal antibody is further separated on SDS-PAGE. Isolated bands are digested in situ in the gel or eluted from the gel and digested with any of a number of proteases, such as trypsin. The digestion produces peptides that can be separated by LC, analyzed for mass by mass spectroscopy, and fragmented by collision in a mass spectroscope. Known degradation products can then identify the peptides and their amino acid sequences. By using more than one protease, these peptides can be ordered and a complete or nearly complete amino acid sequence can be determined.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

What is claimed is:

1. A method of obtaining from CHO cells that recombinantly produce NGAL a composition comprising a plurality of isoforms of NGAL, which method comprises enriching NGAL in a composition, which is obtained from CHO cells that recombinantly produce NGAL, without separating molecules based on charge, by acidifying the composition and extracting the composition with ethanol and zinc acetate, whereupon a composition comprising a plurality of isoforms of NGAL is obtained from CHO cells that recombinantly produce NGAL.

2. The method of claim 1, which further comprises treating the composition after extraction with ethanol and zinc acetate by ultra-filtration buffer exchange, size-exclusion chromatography, and/or ammonium sulfate precipitation.

3. The method of claim 1, wherein the composition comprises at least about seven isoforms of NGAL.

4. The method of claim 1, wherein the composition comprises at least about seven isoforms of NGAL comprising an isoform having a pI of about 5.6, an isoform having a pI of about 5.9, an isoform having a pI of about 6.3, an isoform having a pI of about 6.5, an isoform having a pI of about 6.8, an isoform having a pI of about 7.5, and an isoform having a pI of about 9.1.

5. The method of claim 2, wherein the composition comprises at least about seven isoforms of NGAL.

6. The method of 2, wherein the composition comprises at least about seven isoforms of NGAL comprising an isoform having a pI of about 5.6, an isoform having a pI of about 5.9, an isoform having a pI of about 6.3, an isoform having a pI of about 6.5, an isoform having a pI of about 6.8, an isoform having a pI of about 7.5, and an isoform having a pI of about 9.1.

* * * * *